United States Patent
Bonk et al.

[11] Patent Number: 6,013,340
[45] Date of Patent: Jan. 11, 2000

[54] MEMBRANES OF POLYURETHANE BASED MATERIALS INCLUDING POLYESTER POLYOLS

[75] Inventors: Henry W. Bonk, Wallingford, Conn.; David Goldwasser, Chesterfield, Mo.

[73] Assignee: Nike, Inc., Beaverton, Oreg.

[*] Notice: This patent issued on a continued prosecution application filed under 37 CFR 1.53(d), and is subject to the twenty year patent term provisions of 35 U.S.C. 154(a)(2).

[21] Appl. No.: 08/571,160

[22] Filed: Dec. 12, 1995

Related U.S. Application Data

[63] Continuation-in-part of application No. 08/475,275, Jun. 7, 1995, abandoned.

[51] Int. Cl.[7] .............................. B29D 22/00; B32B 27/40
[52] U.S. Cl. ...................... 428/35.2; 428/35.4; 428/35.5; 428/35.7; 428/36.8; 428/339; 428/423.1; 428/423.5; 428/423.7; 428/424.4; 428/424.6
[58] Field of Search ................... 428/35.7, 36.8, 428/423.1, 424.4, 35.4, 35.5, 35.2, 339, 423.7, 423.5; 36/28, 29, 35 R, 35 B; 5/706, 707, 655.3; 138/30; 297/452.48; 152/157, 155, 246, 450

[56] References Cited

U.S. PATENT DOCUMENTS

| | | | |
|---|---|---|---|
| 3,718,494 | 2/1973 | Jacobson | 106/415 |
| 4,082,854 | 4/1978 | Yamada et al. | 426/106 |
| 4,257,176 | 3/1981 | Hartung et al. | 36/44 |
| 4,340,626 | 7/1982 | Rudy | 428/35.7 |
| 4,344,987 | 8/1982 | Ostertag et al. | 427/213 |
| 4,423,185 | 12/1983 | Matsumoto et al. | 525/66 |
| 4,429,076 | 1/1984 | Saito et al. | 525/57 |
| 4,501,790 | 2/1985 | Aizawa et al. | 428/301.1 |
| 4,513,058 | 4/1985 | Martin | 422/336 |
| 4,536,425 | 8/1985 | Hekal | 428/36.4 |
| 4,551,518 | 11/1985 | Matsumoto et al. | 528/80 |
| 4,557,859 | 12/1985 | Maeda et al. | 252/511 |
| 4,610,099 | 9/1986 | Signori | 36/313 |
| 4,614,208 | 9/1986 | Skarelius | 138/103 |
| 4,681,797 | 7/1987 | Van Isegham | 428/212 |
| 4,692,361 | 9/1987 | Johnston et al. | 428/35.4 |
| 4,722,131 | 2/1988 | Huang | 29/450 |
| 4,731,289 | 3/1988 | Coleman | 428/423.1 |
| 4,786,685 | 11/1988 | Takida et al. | 525/58 |
| 4,864,738 | 9/1989 | Horovitz | 36/29 |
| 4,887,367 | 12/1989 | Mackness et al. | 36/28 |
| 4,927,689 | 5/1990 | Markiewicz | 428/348 |
| 4,936,029 | 6/1990 | Rudy | 36/29 |
| 4,960,639 | 10/1990 | Oda et al. | 428/34.5 |
| 4,978,394 | 12/1990 | Ostertag et al. | 106/404 |
| 4,999,229 | 3/1991 | Moritani et al. | 428/36.6 |
| 5,003,002 | 3/1991 | Ofstein | 525/58 |
| 5,030,404 | 7/1991 | Bonnebat et al. | 264/185 |
| 5,036,110 | 7/1991 | Moureaux | 521/137 |
| 5,036,603 | 8/1991 | Dischler | 36/44 |
| 5,042,176 | 8/1991 | Rudy | 36/29 |
| 5,053,455 | 10/1991 | Kroggel et al. | 525/58 |
| 5,059,245 | 10/1991 | Phillips et al. | 106/31.65 |
| 5,090,010 | 2/1992 | Takahashi | 369/291 |
| 5,096,756 | 3/1992 | Walters | 428/35.5 |
| 5,157,082 | 10/1992 | Johnson | 525/237 |
| 5,215,124 | 6/1993 | Hattori et al. | 138/30 |
| 5,246,761 | 9/1993 | Sasaki | 428/156 |
| 5,292,824 | 3/1994 | Nagai et al. | 525/399 |
| 5,300,334 | 4/1994 | Niederst et al. | 428/423.7 |
| 5,332,767 | 7/1994 | Reisser et al. | 523/209 |
| 5,346,950 | 9/1994 | Negi et al. | 525/57 |
| 5,393,832 | 2/1995 | Moulies et al. | 525/57 |
| 5,409,041 | 4/1995 | Yoshida et al. | 138/30 |
| 5,416,988 | 5/1995 | Potter et al. | 36/89 |
| 5,429,852 | 7/1995 | Quinn | 428/71 |
| 5,436,295 | 7/1995 | Nishikawa et al. | 525/92 C |
| 5,456,787 | 10/1995 | Myles | 156/321 |
| 5,458,935 | 10/1995 | Alzner | 428/35.7 |
| 5,462,980 | 10/1995 | Bastioli et al. | 524/47 |
| 5,489,455 | 2/1996 | Nugent, Jr. et al. | 428/36.91 |
| 5,498,662 | 3/1996 | Tanaka et al. | 525/54.2 |
| 5,532,284 | 7/1996 | Bartlett et al. | 521/134 |
| 5,540,770 | 7/1996 | Schmid et al. | 106/415 |
| 5,567,489 | 10/1996 | Allen et al. | 428/34.1 |
| 5,578,372 | 11/1996 | Murakami | 428/336 |
| 5,591,798 | 1/1997 | Patel | 524/514 |
| 5,601,889 | 2/1997 | Chundury et al. | 428/34.3 |
| 5,609,962 | 3/1997 | Ouhadi | 428/480 |
| 5,612,101 | 3/1997 | Furuta et al. | 428/1 |

| | | |
|---|---|---|
| 5,633,065 | 5/1997 | Matsukura et al. ............... 428/42 |
| 5,645,923 | 7/1997 | Matsuo et al. .................. 428/216 |
| 5,662,738 | 9/1997 | Schmid et al. ................. 106/404 |
| 5,693,424 | 12/1997 | Watanabe et al. ............. 428/424.7 |
| 5,700,560 | 12/1997 | Kotani et al. ................. 428/325 |

FOREIGN PATENT DOCUMENTS

| | | |
|---|---|---|
| 2636638 | 3/1990 | France . |
| 58-22163 | 2/1983 | Japan . |
| 59-196706 | 11/1984 | Japan . |
| 59-116145 | 5/1987 | Japan . |

*Primary Examiner*—Rena L. Dye
*Attorney, Agent, or Firm*—Harness, Dickey & Pierce, P.L.C.

[57] ABSTRACT

The present invention relates to membranes including an urethane including a polyester polyol, wherein the membrane has a gas transmission rate of 15.0 or less for nitrogen gas wherein the membrane has an average thickness of approximately 20.0 mils. Under certain embodiments, the membranes include blends of one or more polyester polyol based thermoplastic urethanes and one or more barrier materials. The membranes can be employed in a variety of applications and can be used as either monolayers or multi-layered laminates.

61 Claims, 8 Drawing Sheets

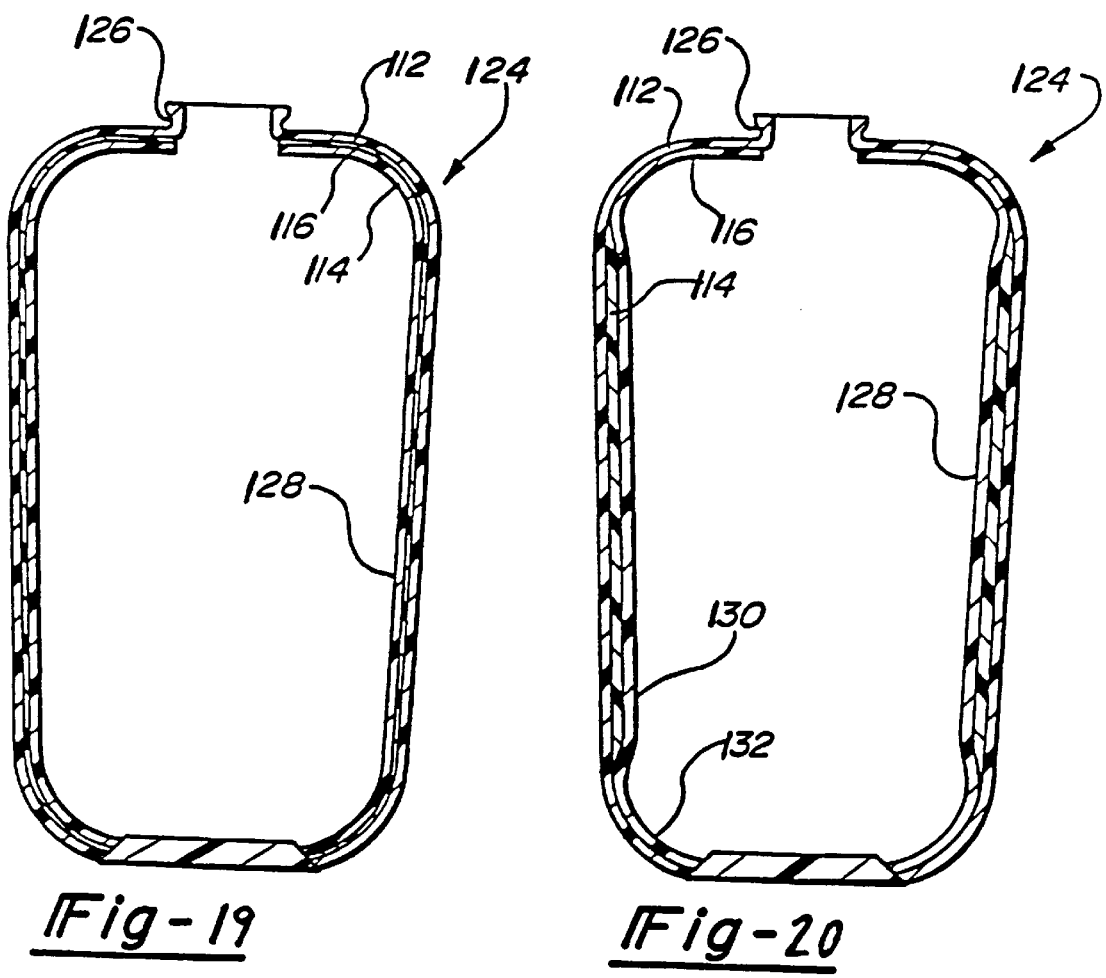

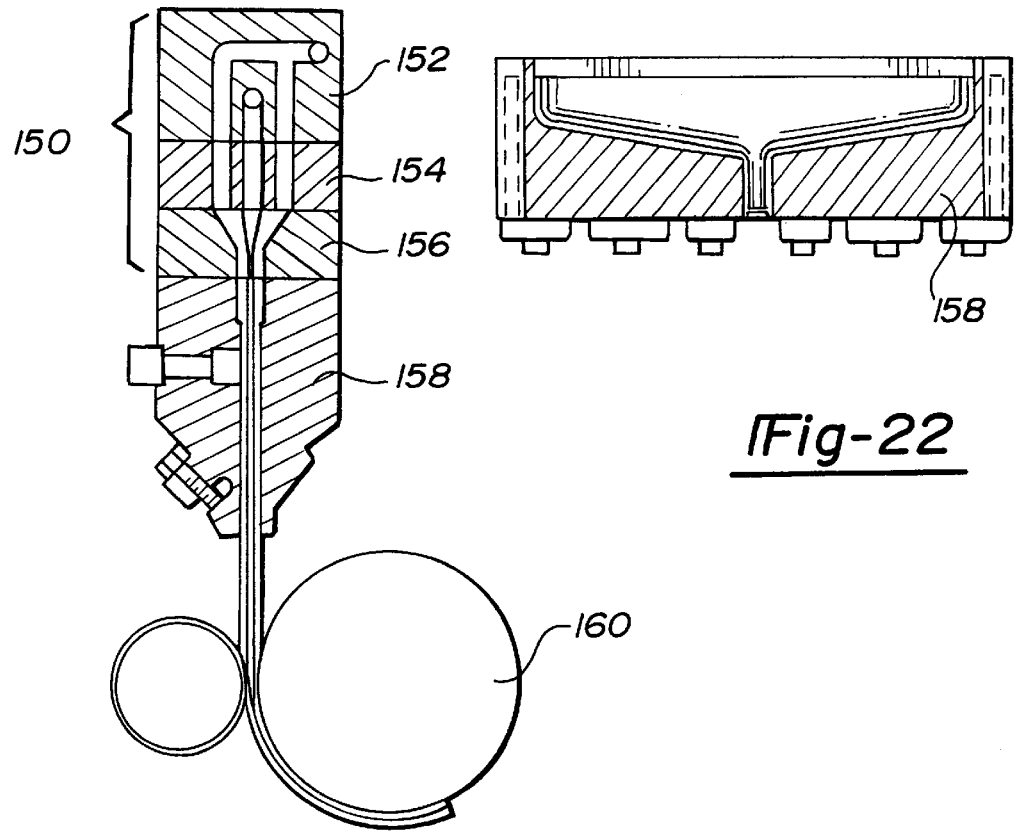
Fig-22
Fig-21
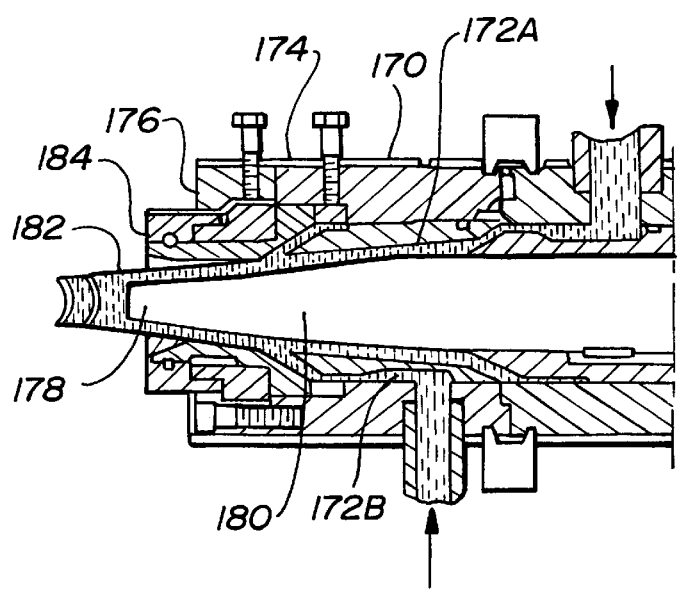
Fig-23

MEMBRANES OF POLYURETHANE BASED MATERIALS INCLUDING POLYESTER POLYOLS

FIELD OF THE INVENTION

The present application is a continuation-in-part of U.S. patent application Ser. No. 08/475,275 entitled "Membranes Including A Barrier Layer Employing Polyester Polyols," filed on Jun. 7, 1995, now abandoned, which is hereby expressly incorporated herein by reference.

The present invention relates to membranes and, more particularly, to membranes which, under certain embodiments, serve to selectively control the diffusion of gases through the membrane. Additionally, the membrane not only selectively controls the diffusion of gases through the membrane, but also allows for the controlled diffusion of gases normally contained in the atmosphere.

BACKGROUND OF THE INVENTION

Membranes, and more particularly, membranes useful for containing fluids, including liquids and/or gases, in a controlled manner, have been employed for years in a wide variety of products ranging from bladders useful in inflatable objects, including vehicle tires and sporting goods for example; to accumulators used on heavy machinery; to cushioning devices useful in footwear. Regardless of the intended use, membranes must generally be flexible, resistant to environmental degradation and exhibit excellent gas transmission controls. Often, however, materials which exhibit acceptable flexibility characteristics tend to have an unacceptably low level of resistance to gas permeation. In contrast, materials which exhibit an acceptable level of resistance to gas permeation tend to have an unacceptably low level of flexibility.

In an attempt to address the concerns of both flexibility and imperviousness to gases, U.S. Pat. No. 5,036,110 which issued Jun. 30, 1991, to Moreaux describes resilient membranes for fitting hydropneumatic accumulators. According to Moreaux '110, the membrane disclosed consists of a film formed from a graft polymer which is the reaction product of an aromatic thermoplastic polyurethane with a copolymer of ethylene and vinyl alcohol, with this film being sandwiched between layers of thermoplastic polyurethane to form a laminate. While Moreaux '110 attempts to address the concerns in the art relating to flexibility and imperviousness to gases, a perceived drawback of Moreaux is that the film described is not processable utilizing conventional techniques such as sheet extrusion, for example. Thus, the present invention is directed to membranes which are flexible, have good resistance to gas transmission, and under certain embodiments are processable into laminates utilizing conventional techniques such as sheet extrusion which are highly resistant to delamination.

While it should be understood by those skilled in the art upon review of the following specification and claims that the membranes of the present invention have a broad range of applications, including but not limited to bladders for inflatable objects such as footballs, basketballs, soccer balls, inner tubes; substantially rigid flotation devices such as boat hulls; flexible floatation devices such as tubes or rafts; as a component of medical equipment such as catheter balloons; fuel lines and fuel storage tanks; various cushioning devices such as those incorporated as part of an article of footwear or clothing; as part of an article of furniture such as chairs and seats, as part of a bicycle or saddle, as part of protective equipment including shin guards and helmets; as a supporting element for articles of furniture and, more particularly, lumbar supports; as part of a prosthetic or orthopedic device; as a portion of a vehicle tire and particularly, the outer layer of the tire, as well as being incorporated as part of certain recreation equipment such as components of wheels for in-line or roller skates, to name a few, still other applications are possible. For example, one highly desirable application for the membranes of the present invention include their use in forming accumulators which are operable under high pressure environments such as hydraulic accumulators as will be discussed in greater detail below.

For convenience, but without limitation, the membranes of the present invention will hereinafter generally be described in terms of either accumulators or in terms of still another highly desirable application, namely for cushioning devices used in footwear. In order to fully discuss the applicability of the membranes in terms of cushioning devices for footwear, a description of footwear in general is believed to be necessary.

Footwear, or more precisely, shoes generally include two major categories of components namely, a shoe upper and the sole. The general purpose of the shoe upper is to snugly and comfortably enclose the foot. Ideally, the shoe upper should be made from an attractive, highly durable, yet comfortable material or combination of materials. The sole, which also can be made from one or more durable materials, is particularly designed to provide traction and protect the wearer's feet and body during use. The considerable forces generated during athletic activities require that the sole of an athletic shoe provide enhanced protection and shock absorption for the feet, ankles and legs of the wearer. For example, impacts which occur during running activities can generate forces of up to 2–3 times the body weight of an individual while certain other activities such as, for example, playing basketball have been known to generate forces of up to approximately 6–10 times an individual's body weight. Accordingly, many shoes and, more particularly, many athletic shoes are now provided with some type of resilient, shock-absorbent material or shock-absorbent components to cushion the user during strenuous athletic activity. Such resilient, shock-absorbent materials or components have now commonly come to be referred to in the shoe manufacturing industry as the midsole.

It has therefore been a focus of the industry to seek midsole designs which achieve an effective impact response in which both adequate shock absorption and resiliency are appropriately taken into account. Such resilient, shock-absorbent materials or components could also be applied to the insole portion of the shoe, which is generally defined as the portion of the shoe upper directly underlining the plantar surface of the foot.

A particular focus in the footwear manufacturing industry has been to seek midsole or insert structure designs which are adapted to contain fluids, in either the liquid or gaseous state, or both. Examples of gas-filled structures which are utilized within the soles of shoes are shown in U.S. Pat. No. 900,867 entitled "Cushion for Footwear" which issued Oct. 13, 1908, to Miller; U.S. Pat. No. 1,069,001 entitled "Cushioned Sole and Heel for Shoes" which issued Jul. 29, 1913, to Guy; U.S. Pat. No. 1,304,915 entitled "Pneumatic Insole" which issued May 27, 1919, to Spinney; U.S. Pat. No. 1,514,468 entitled "Arch Cushion" which issued Nov. 4, 1924, to Schopf; U.S. Pat. No. 2,080,469 entitled "Pneumatic Foot Support" which issued May 18, 1937, to Gilbert; U.S. Pat. No. 2,645,865 entitled "Cushioning Insole for Shoes" which issued Jul. 21, 1953, to Towne; U.S. Pat. No. 2,677,906 entitled "Cushioned Inner Sole for Shoes and Method of Making the Same" which issued May 11, 1954, to Reed; U.S. Pat. No. 4,183,156 entitled "Insole Construction for Articles of Footwear" which issued Jan. 15, 1980, to Rudy; U.S. Pat. No. 4,219,945 entitled "Footwear" which issued Sep. 2, 1980, also to Rudy; U.S. Pat. No. 4,722,131 entitled "Air Cushion Shoe Sole" which issued Feb. 2, 1988, to Huang; and U.S. Pat. No. 4,864,738 entitled "Sole Construction for Footwear" which issued Sep. 12, 1989, to Horovitz. As will be recognized by those skilled in the art, such gas filled structures often referred to in the shoe manufacturing industry as "bladders" typically fall into two broad categories, namely (1) "permanently" inflated systems such as those disclosed in U.S. Pat. Nos. 4,183,156 and 4,219,945 and (2) pump and valve adjustable systems as exemplified by U.S. Pat. No. 4,722,131. By way of further example, athletic shoes of the type disclosed in U.S. Pat. No. 4,182,156 which include "permanently" inflated bladders have been successfully sold under the trade mark "Air-Sole" and other trademarks by Nike, Inc. of Beaverton, Oreg. To date, millions of pairs of athletic shoes of this type have been sold in the United States and throughout the world.

The permanently inflated bladders have historically been constructed under methods using a flexible thermoplastic material which is inflated with a large molecule, low solubility coefficient gas otherwise referred to in the industry as a "super gas." By way of example, U.S. Pat. No. 4,340,626 entitled "Diffusion Pumping Apparatus Self-Inflating Device" which issued Jul. 20, 1982, to Rudy, which is expressly incorporated herein by reference, discloses selectively permeable sheets of film which are formed into a bladder and thereafter inflated with a gas or mixture of gases to a prescribed pressure which preferably is above atmospheric pressure. The gas or gases utilized ideally have a relatively low diffusion rate through the selectively permeable bladder to the exterior environment while gases such as nitrogen, oxygen and argon which are contained in the atmosphere and have a relatively high diffusion rate are able to penetrate the bladder. This produces an increase in the total pressure within the bladder, by the addition of the partial pressures of the nitrogen, oxygen and argon from the atmosphere to the partial pressures of the gas or gases contained initially injected into the bladder upon inflation. This concept of a relative one-way addition of gases to enhance the total pressure of the bladder is now known as "diffusion pumping."

With regard to the systems utilized within the footwear manufacturing industry prior to and shortly after the introduction of the Air-Solen™ athletic shoes, many of the midsole bladders consisted of a single layer gas barrier type films made from polyvinylidene chloride based materials such as Saran® (which is a registered trademark of the Dow Chemical Co.) and which by their nature are rigid plastics, having relatively poor flex fatigue, heat sealability and elasticity.

Still further, bladder films made under techniques such as laminations and coatings which involve one or more barrier materials in combination with a flexible bladder material (such as various thermoplastics) can potentially present a wide variety of problems to solve. Such difficulties with composite constructions include layer separation, peeling, gas diffusion or capillary action at weld interfaces, low elongation which leads to wrinkling of the inflated product, cloudy appearing finished bladders, reduced puncture resistance and tear strength, resistance to formation via blow-molding and/or heat-sealing and RF welding, high cost processing, and difficulty with foam encapsulation and adhesive bonding, among others.

Yet another issue with previously known multi-layer bladders is the use of tie-layers or adhesives in preparing laminates. The use of such tie layers or adhesives generally prevent regrinding and recycling of any waste materials created during product formation back into an usable product, and thus, also contribute to high cost of manufacturing and relative waste. These and other perceived short comings of the prior art are described in more extensive detail in U.S. Pat. Nos. 4,340,626; 4,936,029 and 5,042,176, all of which are hereby expressly incorporated by reference.

Previously known multi-layer bladders which specifically eliminate adhesive tie layers have been known to separate or de-laminate especially along seams and edges. Thus, it has been a relatively recent focus of the industry to develop laminated bladders which reduce or eliminate the occurrence of delamination ideally without the use of a "tie layer." In this regard, the cushioning devices disclosed in co-pending U.S. application patent Ser. Nos. 08/299,286 and 08/299,287 eliminate adhesive tie layers by providing membranes including a first layer of thermoplastic urethane and a second layer including a barrier material such as a copolymer of ethylene and vinyl alcohol wherein hydrogen bonding occurs over a segment of the membranes between the first and second layers. While the membranes disclosed in U.S. patent application Ser. No. 08/299,287 and the laminated flexible membranes of U.S. patent application Ser. No. 08/299,286 are believed to offer a significant improvement in the art, still further improvements are offered according to the teachings of the present invention.

With the extensive commercial success of the products such as the Air-Sole™ shoes, consumers have been able to enjoy products with a long service life, superior shock absorbency and resiliency, reasonable cost, and inflation stability, without having to resort to pumps and valves. Thus, in light of the significant commercial acceptance and success that has been achieved through the use of long life inflated gas filled bladders, it is highly desirable to develop advancements relating to such products. One goal then is to provide flexible, "permanently" inflated, gas-filled shoe cushioning components which meet, and hopefully exceed, performance achieved by such products as the Air-Sole™ athletic shoes offered by Nike, Inc.

An accepted method of measuring the relative permeance, permeability and diffusion of different film materials is set forth in the procedure designated as ASTM D-1434-82-V. According to ASTM D-1434-82-V, permeance, permeability and diffusion are measured by the following formulas:

Permeance $$\frac{\text{(quantity of gas)}}{\text{(area)} \times \text{(time)} \times \text{(press. diff.)}} = \text{Permeance (GTR)/(press. diff.)} = \frac{\text{cc.}}{\text{(sq.m)(24 hr) (Pa)}}$$

Permeability $$\frac{\text{(quantity of gas)} \times \text{(film thick)}}{\text{(area)} \times \text{(time)} \times \text{(press. diff.)}} = \frac{\text{Permeability}}{\text{(GTR)} \times \text{(film thick)} / \text{(press. diff.)}} = \frac{\text{(cc) (mil)}}{\text{(sq.m) (24 hr) (Pa)}}$$

Diffusion $$\frac{\text{(quantity of gas)}}{\text{(area)} \times \text{(time)}} = \frac{\text{Gas Transmission Rate}}{\text{(GTR)}} = \frac{\text{cc}}{\text{(sq.m) (24 hr)}}$$

By utilizing the above listed formulas, the gas transmission rate in combination with a constant pressure differential and the film's thickness, can be utilized to define the movement of gas under specific conditions. In this regard, the preferred gas transmission rate (GTR) for a membrane having an average thickness of approximately 20.0 mils such as those useful for forming a cushioning device used as a shoe component which seeks to meet the rigorous demands of fatigue resistance imposed by heavy and repeated impacts will preferably have a gas transmission rate (GTR) of 15.0 or less for nitrogen gas according to ASTM D-1434-82-V. More preferably, the membranes will have a GTR of less than about 2.0 at an average thickness of 20 mils.

It is, therefore, one object of the present invention to provide membranes including both single layer and multi-layer constructions which offer enhanced flexibility, durability and resistance to the undesired transmission of fluids therethrough.

It is another object of the present invention to provide membranes which can be inflated with a gas such as nitrogen wherein the membrane provides for a gas transmission rate value of 15.0 or less, based on a 20 mils average thickness.

It is still another object of the present invention to provide membranes, particularly those employed as cushioning devices, having a relatively high degree of transparency.

It is another object of the present invention to provide monolayer membranes which are readily processable into various products.

It is yet another object of the present invention to provide monolayer membranes and, under certain applications, multi-layer membranes which are reprocessable and repairable.

It is yet another object of the present invention to provide membranes which can be formed into laminated objects such as cushioning devices or accumulators, among others, which better resist delamination and also may not require a tie layer between the layers.

It is a further object of the present invention to provide membranes which are formable utilizing various techniques including, but not limited to, blow-molding, tubing, sheet extrusion, vacuum-forming, heat-sealing, casting, liquid casting, low pressure casting, spin casting, reaction injection molding and RF welding.

Still another object of the present invention is to provide membranes which prevent gas from escaping along interfaces between the layers in laminated embodiments and particularly along seams via capillary action.

It is yet another object of the present invention to provide a membrane which allows for footwear processing such as encapsulation of a membrane within a formable material.

While the aforementioned objects provide guidance as to possible applications and advantages for the membranes of the present invention, it should be recognized by those skilled in the art that the recited objects are not intended to be exhaustive or limiting.

SUMMARY OF THE INVENTION

To achieve the foregoing objects, the present invention provides membranes which preferably have one or more of the following: (1) a desirable level of flexibility (or rigidity); (2) a desirable level of resistance to degradation caused by moisture; (3) an acceptable level of imperviousness to fluids which can be in the form of gases, liquids or both depending mainly on the intended use of the product; and (4) resistance to delamination when employed in a multi-layer structure. Regardless of the membrane embodiment, each membrane in accordance with the teachings of the present invention includes a layer comprised of a polyester polyol based polyurethane. The aforementioned layer may also include at least one barrier material selected from the group consisting of co-polymers of ethylene and vinyl alcohol, polyvinylidene chloride, co-polymers of acrylonitrile and methyl acrylate, polyethylene terephthalate, aliphatic and aromatic polyamides, crystalline polymers and polyurethane engineering thermoplastics blended with the polyurethane prior to forming the membranes.

The polyester polyol based urethanes employed, if not commercially available, are preferably formed as the reaction product of (a) one or more carboxylic acids having six or less carbon atoms with one or more diols having six or less carbon atoms; (b) at least one isocyanate and/or diisocyanate; and (c) optionally, but preferably, one or more extenders. The polyester polyol may also include a relatively small amount of one or more polyfunctional materials such as triols which are included as part of the reaction product. In addition to the foregoing, the polyester polyol based urethanes may optionally employ one or more of the following: (d) hydrolytic stabilizers; (e) plasticizers; (f) fillers; (g) flame retardants; and (h) processing aids. The resulting polyester polyols formed as a result of the reaction product of the one or more carboxylic acids with one or more diols preferably have repeating units containing eight carbon atoms or less.

The term "carboxylic acid" as used herein, and unless otherwise indicated, preferably means a carboxylic acid, and more preferably a dicarboxylic acid, having no more than six carbon atoms when reacted with a diol, wherein the repeating units of the polyester polyol formed by the aforesaid reaction has no more than eight carbon atoms.

The term "diol" as used herein, and unless otherwise indicated, to preferably mean diols having no more than six carbon atoms when reacted with a carboxylic acid, wherein the repeating units of the polyester polyol formed by the aforesaid reaction has no more than eight carbon atoms.

The term "polyester polyol" as used herein is intended to preferably mean polymeric polyester polyols having a molecular weight (determined by the ASTM D-4274 method) falling in the range of about 300 to about 4,000; more preferably from about 400 to about 2,000; and still more preferably between about 500 to about 1,500.

The term "thermoplastic" as used herein is generally intended to mean that the material is capable of being softened by heating and hardened by cooling through a characteristic temperature range, and as such in the softened state can be shaped into various articles under various techniques.

The term "thermoset" as used herein is generally intended to mean a polymeric material that will not flow upon the application of heat and pressure after it is substantially reacted.

The term "extender" or "difunctional extender" is used preferably in the commonly accepted sense to one skilled in the art and includes glycols, diamines, amino alcohols and the like. Preferably, any such extender or difunctional extender employed in accordance with the teachings of the present invention will have a molecular weight generally falling in the range of from about 60 to about 400.

The term "soft segment" as used herein is generally intended to mean the component of the formulation exhibiting a molecular weight from approximately 300–4000 that contains approximately two or more active hydrogen groups per molecule prior to reaction that provides the elastomeric character of the resulting polymers.

Preferably, the membranes described herein may be useful as components for footwear. In such applications, the membranes preferably are capable of containing a captive gas for a relatively long period of time. In a highly preferred embodiment, for example, the membrane should not lose more than about 20% of the initial inflated gas pressure over a period of approximately two years. In other words, products inflated initially to a steady state pressure of between 20.0 to 22.0 psi should retain pressure in the range of about 16.0 to 18.0 psi for at least about two years.

Additionally, the materials utilized for products such as components of athletic shoes should be flexible, relatively soft and compliant and should be highly resistant to fatigue and be capable of being welded to form effective seals typically achieved by RF welding or heat sealing. The material should also have the ability to withstand high cycle loads without failure, especially when the material utilized has a thickness of between about 5 mils to about 200 mils.

Another preferred characteristic of the membrane is the ability to be processable into various shapes by techniques used in high volume production. Among these techniques known in the art are extrusion, blow molding, injection molding, vacuum molding, rotary molding, transfer molding, pressure forming, heat-sealing, casting, low pressure casting, spin casting, reaction injection molding and RF welding, among others.

As discussed above, a preferred characteristic of the membranes, whether monolayer or multi-layer in construction, is their ability under embodiments to be formed into products which are inflated (such as cushioning devices for footwear) and which control diffusion of mobile gases through the membrane. By the present invention, not only are super gases usable as captive gases, but nitrogen gas and air, among others, may also be used as captive gases due to the performance of the materials.

Another feature of the monolayer membranes of the present invention is elimination of many of the processing concerns presented by multi-layer embodiments. Monolayer membranes can generally be processed without requiring special mechanical adapters for processing equipment and other process controls. Further, products formed from monolayer embodiments are not subject to delamination and can, at least in the case of thermoplastics, be recycled and reground for subsequent inclusion in a variety of products.

With regard to multiple layer embodiments, a further feature of the present invention is the enhanced bonding which can occur between contiguous layers, thus, potentially eliminating the need for adhesive tie layers. This so-called enhanced bonding is generally accomplished by bringing the first and second layers together into intimate contact using conventional techniques wherein the materials of both layers have available functional groups with hydrogen atoms that can participate in hydrogen bonding such as hydrogen atoms in hydroxyl groups or hydrogen atoms attached to nitrogen atoms in urethane groups and various receptor groups such as oxygen atoms in hydroxyl groups, carboxyl oxygens in urethane groups and ester groups, and chlorine atoms in PVDC, for example. Such laminated membranes are characterized in that hydrogen bonding is believed to occur between the first and second layers. For example, the above described hydrogen bonding will theoretically occur where the first layer comprises a polyester polyol based urethane and the second layer includes a barrier material such as one selected from the group consisting of co-polymers of ethylene and vinyl alcohol, polyvinylidene chloride, co-polymers of acrylonitrile and methyl acrylate, polyethylene terephthalate, aliphatic and aromatic polyamides, crystalline polymers and polyurethane engineering thermoplastics. In addition to the occurrence of hydrogen bonding, it is theorized that there will also generally be a certain amount of covalent bonding between the first and second layers if, for example, there are polyurethanes in adjacent layers or if one of the layers includes polyurethane and the adjacent layer includes a barrier material such as copolymers of ethylene and vinyl alcohol.

This invention has many other advantages which will be more apparent from consideration of the various forms and embodiments of the present invention. Again, while the embodiments shown in the accompanying drawings which form a part of the present specification are illustrative of embodiments employing the membranes of the present invention, it should be clear that the membranes have extensive application possibilities. Various exemplary embodiments will now be described in greater detail for the purpose of illustrating the general principles of the invention, without considering the following detailed description in the limiting sense.

BRIEF DESCRIPTION OF THE DRAWINGS

FIG. 19 is a sectional view of a product formed from a laminated membrane according to the teachings of the present invention;

FIG. 20 is a sectional view of a second product manufactured using a laminated membrane according to the teachings of the present invention;

FIG. 21 is a side elevation view of a sheet co-extrusion assembly;

FIG. 22 is a cross-sectional view of the manifold portion of the sheet co-extrusion assembly of FIG. 22;

FIG. 23 is a side elevation view of a tubing co-extrusion assembly;

DETAILED DESCRIPTION OF THE PREFERRED EMBODIMENTS

Figure 1:
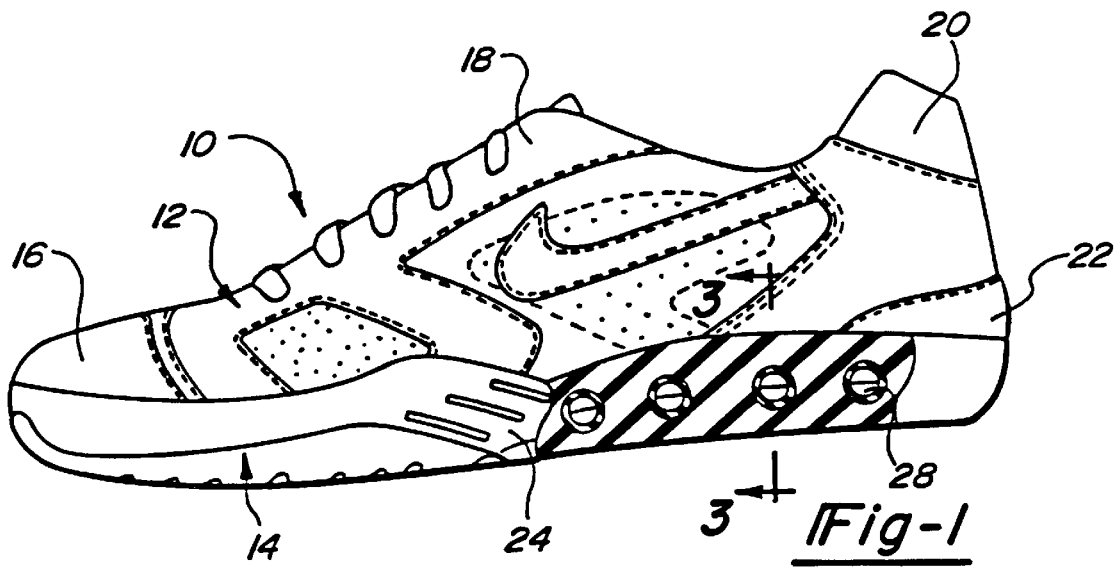
FIG. 1 is a side elevational view of an athletic shoe with a portion of the midsole cut away to illustrate a cross-sectional view.
Figure 2:
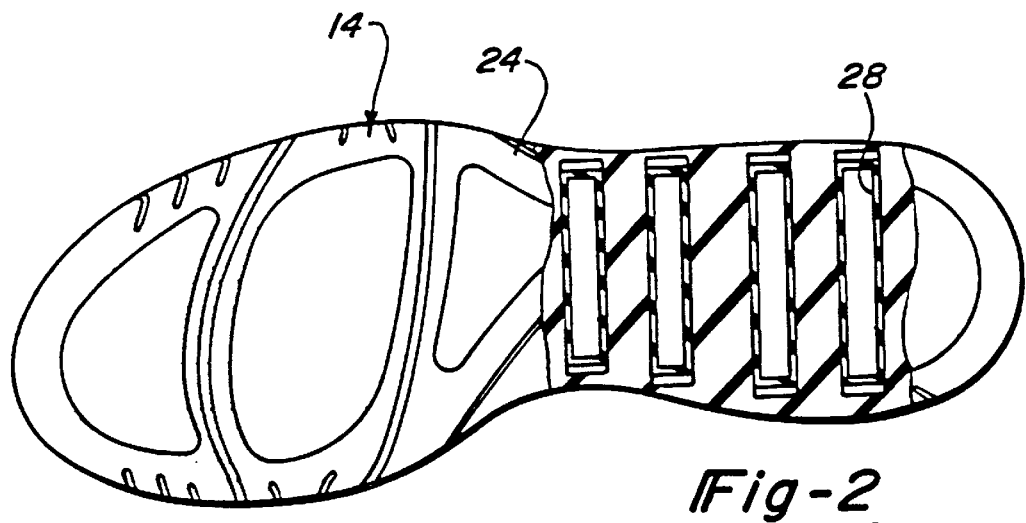
FIG. 2 is a bottom elevational view of the athletic shoe of FIG. 1 with a portion cut away to expose another cross-sectional view.
Figure 3:
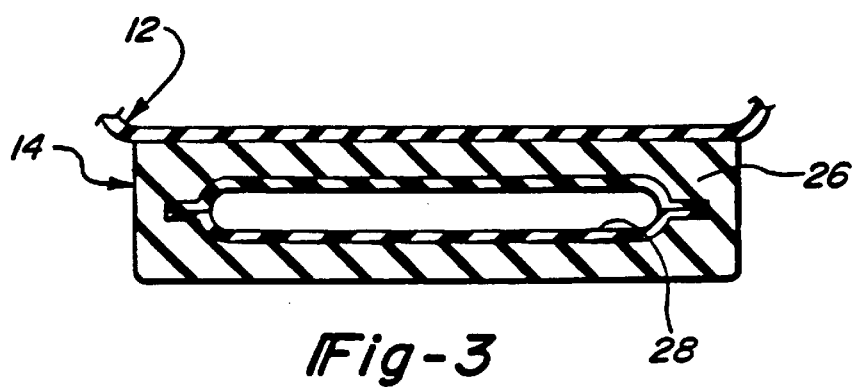
FIG. 3 is a section view taken alone line 3—3 of FIG. 1.

Referring to FIGS. 1–3, there is shown an athletic shoe, including a sole structure and a cushioning device as one example of a product formed from a membrane in accordance with the teachings of the present invention. The shoe 10 includes a shoe upper 12 to which the sole 14 is attached. The shoe upper 12 can be formed from a variety of conventional materials including, but not limited to, leathers, vinyls, nylons and other generally woven fibrous materials. Typically, the shoe upper 12 includes reinforcements located around the toe 16, the lacing eyelets 18, the top of the shoe 20 and along the heel area 22. As with most athletic shoes, the sole 14 extends generally the entire length of the shoe 10 from the toe region 20 through the arch region 24 and back to the heel portion 22.

Figure 4:
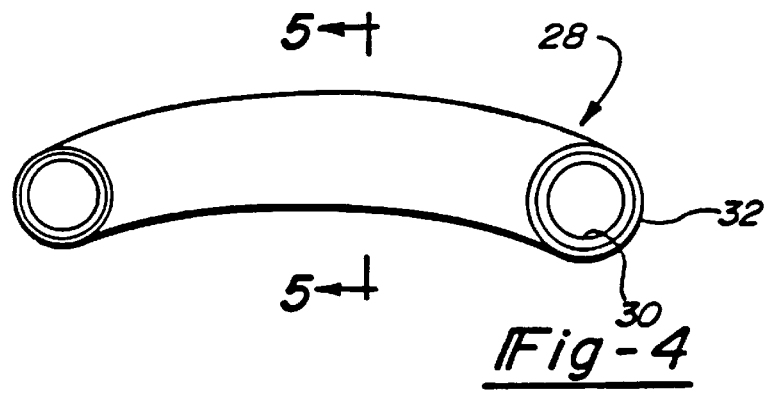
FIG. 4 is a fragmentary side perspective view of one embodiment of a tubular-shaped, two-layer cushioning device.
Figure 5:
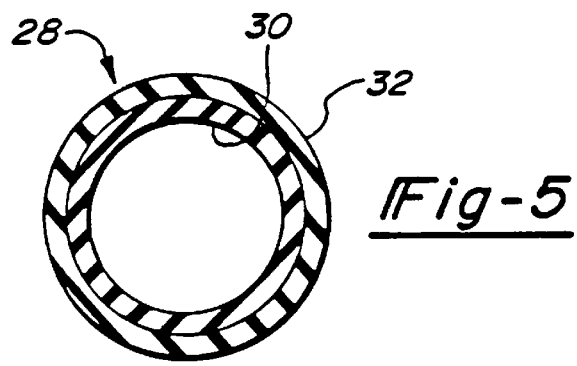
FIG. 5 is a sectional view taken along line 4—4 of FIG. 4.
Figure 24:
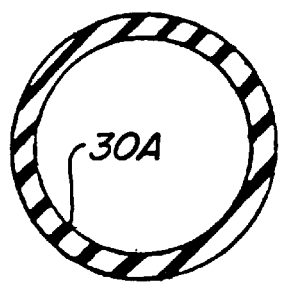
FIG. 24 is a sectional view of a monolayer tubular membrane.

The sole structure 14 is shown to include one or more selectively permeable cushioning devices or membranes 28, which are generally disposed in the midsole of the sole structure. By way of example, the membranes 28 of the present invention can be formed into products having various geometries such as the plurality of tubular members which are positioned in a spaced apart, parallel relationship to each other within the heel region 22 of the midsole 26 as illustrated in FIGS. 1–3. The tubular members are sealed to contain an injected captive gas. The barrier properties of the membrane 28 are preferably provided by a single or monolayer embodiment 30A as shown in FIG. 24 or by the layer 30 as shown in FIGS. 4–5 which is disposed along the inner surface of a thermoplastic outer layer 32. As illustrated in FIGS. 8–18, the membranes 28 of the present invention, whether monolayer or multi-layer embodiments, can be formed into a variety of products having numerous configurations or shapes. As should be appreciated at this point, membranes 28 which are formed into cushioning devices employed in footwear may either be fully or partially encapsulated within the midsole or outsole of the footwear.

Referring again to FIGS. 1–3, a membrane 28 in accordance with teachings of the present invention is illustrated as being in the form of a cushioning device such as those useful as components of footwear. The membrane 28, according to the embodiment illustrated in FIG. 24, comprises a single layer 30A formed from one or more polyester polyol based urethanes. The polyester polyol based urethanes are preferably formed by the reaction product of: (a) one or more carboxylic acids having six or less carbon atoms with one or more diols having six or less carbon atoms; (b) at least one isocyanate and/or diisocyanate; and (c) optionally, but preferably, one or more extenders. Optionally, the polyester polyol based urethanes may also employ one or more of the following: (d) hydrolytic stabilizers; (e) plasticizers; (f) fillers; (g) flame retardants; and (h) processing aids. As previously noted, the polyester polyol is preferably formed as the reaction product of one or more carboxylic acids with one or more diols, wherein the total number of carbon atoms contained in the repeating units of polyester polyol in the reaction product is eight or less. In addition to the one or more diols, the reaction product may also include a relatively small amount of one or more polyfunctional materials such as triols, i.e. no more than 5.0 equivalent percent based on the total for the reaction product and active hydrogen containing groups.

Among the carboxylic acids which are considered to be useful in forming polyester polyol based urethanes under the present invention, those including adipic, glutaric, succinic, malonic, oxalic and mixtures thereof are considered to be particularly useful.

Among the diols which are considered to be useful in forming the polyester polyol based urethanes under the present invention, those including ethylene glycol, propanediol, butanediol, neopentyidiol, pentanediol and hexanediol and mixtures thereof are considered to be particularly useful. Among the triols which are considered useful in forming the polyester polyol based urethanes are those including trimethylolpropane are considered to be particularly useful.

Under preferred embodiments, the polyester polyol based thermoplastic urethane employed in forming layer 30A for monolayer applications and 30 for multi-layer applications will include ethylene glycol adipate. In this regard, certain commercially available ethylene glycol adipates such as FOMREZ® 22-112 and 22-225 available from Witco Chemical are considered to be useful.

Among the isocyanates and, more particularly, diisocyanates employed in accordance with the teachings of the present invention, those including isophorone diisocyanate (IPDI), methylene bis 4-cyclohexyl isocyanate ($H_{12}MDI$), cyclohexyl diisocyanate (CHDI), hexamethylene diisocyanate (HDI), m-tetramethyl xylene diisocyanate (m-TMXDI), p-tetramethyl xylene diisocyanate (P-TMXDI), and xylylene diisocyanate (XDI) are considered to be useful; particularly useful is diphenylmethane diisocyanate (MDI). Preferably, the isocyanate(s) employed are proportioned such that the overall ratio of equivalents of isocyanate to equivalents of active hydrogen containing materials is within the range of 0.95:1 to 1.10:1, and more preferably, 0.98:1 to 1.04:1. As is known in the urethane chemistry art, the phrase "active hydrogen containing groups" generally refers to groups including amines and alcohols collectively, which are capable of reacting with the isocyanate groups.

Optionally, but often preferably, hydrolytic stabilizers will be included in the polyester polyol based polyurethanes of the present invention. For example, two commercially available carbodiimide based hydrolytic stabilizers known as STABAXOL P and STABAXOL P-100, which are available from Rhein Chemie of Trenton, N.J., have proven to be effective at reducing the susceptibility of the material to hydrolysis. Still other hydrolytic stabilizers such as those which are carbodiimide or polycarbodiimide based, or based on epoxidized soy bean oil are considered useful. The total amount of hydrolytic stabilizer employed will generally be less than 5.0 wt. % of the composition's total.

In addition to hydrolytic stabilizers, generally various plasticizers can be included for purposes of increasing the flexibility and durability of the final product as well as facilitating the processing of the material from a resinous form to a membrane or sheet. By way of example, and without intending to be limiting, plasticizers such as those based on butyl benzoyl phthalate have proven to be particularly useful. Regardless of the plasticizer or mixture of plasticizers employed, the total amount of plasticizer, if any, will generally be less than 40.0 wt. % of the composition's total.

Fillers may also be employed in the polyester polyol based polyurethanes of the present invention, especially with regard to monolayer applications wherein hydrogen bonding between layers is not a concern. Included in the class of materials generally referred to herein as "fillers" are fibrous and particulate materials, non-polar polymeric materials and inorganic anti-block agents. Examples of such materials include glass and carbon fibers, glass flakes, silicas, calcium carbonate, clay, mica, talc, carbon black, particulate graphite and metallic flakes, among others. In the event that fillers are employed, generally the total amount of fillers will be less than 60.0 wt. % of the total composition weight.

Yet another class of components which may be employed in the polyester polyol based urethane compositions of the present invention include flame retardants as the term is understood in the art. While the amount of any flame retardants employed is generally dependent upon the desired use of the final product, the total amount of flame retardant contemplated for any application would be 40.0 wt. % or less based on the total weight of the composition. Among the numerous flame retardants which are considered useful, those based on phosphorous or halogenated compounds and antimony oxide based compositions are considered to be particularly useful.

With regard to the use of additives, otherwise referred to herein as processing aids, minor amounts of antioxidants, UV stabilizers, thermal stabilizers, light stabilizers, organic anti-block compounds, colorants, fungicides, mold release agents and lubricants as are known in the art may be employed wherein the total constituency of all such processing aids is generally less than 3.0 wt. %.

It may also be desirable to include a catalyst in the reaction mixture to prepare the compositions of the present invention. Any of the catalysts conventionally employed in the art to catalyze the reaction of an isocyanate with a reactive hydrogen containing compound can be employed for this purpose; see, for example, Saunders et al., Polyurethanes, Chemistry and Technology, Part I, Interscience, New York, 1963, pages 228–232; see also, Britain et al., J. Applied Polymer Science, 4, 207–211, 1960. Such catalysts include organic and inorganic acid salts of, and organometallic derivatives of, bismuth, lead, tin, iron, antimony, uranium, cadmium, cobalt, thorium, aluminum, mercury, zinc, nickel, cerium, molybdenum, vanadium, copper, manganese and zirconium, as well as phosphines and tertiary organic amines. Representative organotin catalysts are stannous octoate, stannous oleate, dibutyltin dioctoate, dibutyltin dilaurate, and the like. Representative tertiary organic amine catalysts are triethylamine, triethylenediamine, $N_1N_1N'_1N'$-tetramethylethylenediamine, $N_1N_1N'_1N'$-tetraethylethylenediamine, N-methyl-morpholine, N-ethylmorpholine, $N_1N_1N'_1N'$-tetramethylguanidine, and $N_1N_1N'_1N'$-tetramethyl-1,3-butanediamine.

Regardless of the catalyst(s) which is utilized, if any, the weight percentage of such material is typically less than one half of one percent by weight (0.5 wt. %) based on the total weight of the polyester polyol based thermoplastic urethane reaction mixture.

Among the extenders which are optionally, but preferably, employed in accordance with the teachings of the present inventions are those generally selected from the group consisting of alcohols and amines. For example, alcohol based extenders may include ethylene glycol, 1,3-propylene glycol, 1,2-propylene glycol, 1,4-butanediol, 1,6-hexanediol, neopentyl glycol, and the like; and dihydroxy-alkylated aromatic compounds such as the bis (2-hydroxyethyl) ethers of hydroquinone and resorcinol; p-xylene-α,α'-diol; the bis (2-hydroxyethyl) ether of p-xylene-α,α'-diol; m-xylene-α,α'-diol and the bis (2-hydroxyethyl) ether and mixtures thereof. Illustrative of diamine extenders are aromatic diamines such as p-phenylenediamine, m-phenylenediamine, benzidine, 4,4'-methylenedianiline, 4,4'-methylenibis (2-chloroaniline) and the like. Illustrative of aliphatic diamine extenders is ethylene diamine. Illustrative of amino alcohols are ethanolamine, propanolamine, butanolamine, and the like.

Preferred extenders include ethylene glycol, 1,3-propylene glycol, 1,4-butanediol, 1,6-hexanediol, and the like.

In addition to the above-described extenders, a small amount of trifunctional extenders such as trimethylol propane, 1,2,6 hexanetriol and glycerol, may also be present. The amount of trifunctional extenders employed would preferably be 5.0 equivalent percent or less based on the total weight of the reaction product and active hydrogen containing groups employed.

Generally, the ratio of polyester polyol to extender can be varied within a relatively wide range depending largely on the desired hardness of the final polyurethane elastomer. As such, the equivalent proportion of polyester polyol to extender should be within the range of 1:0 to 1:12 and, more preferably, from 1:1 to 1:8.

In addition to the at least one polyester polyol based urethane, the layer 30A of FIG. 24 may contain one of the following and layer 30 of FIGS. 4 and 5 will also preferably contain one or more materials selected from the group consisting of co-polymers of ethylene and vinyl alcohol, polyvinylidene chloride, co-polymers of acrylonitrile and methyl acrylate, polyethylene terephthalate, aliphatic and aromatic polyamides, crystalline polymers and polyurethane engineering thermoplastics. Such materials are preferably blended with the polyester polyol based urethane constituent utilizing conventional blending techniques prior to forming the membranes.

For monolayer embodiments 30A, it is preferred that the total amount of one or more of the above listed materials be up to about 30.0 wt. %, since higher amounts tend to result in products which are somewhat inflexible. In multi-layer embodiments, however, the total amount of one or more of the above listed materials in a blended layer may be up to about 95.0 wt. %. Thus, for multi-layer constructions, layer 30 which preferably employs blends of at least one polyester polyol based urethane and one or more of the above-listed materials will generally include up to 70.0 wt. % polyester polyol based thermoplastic urethane but, more preferably, will include between about 1.0 wt. % to about 50.0 wt. % polyester polyol based thermoplastic urethanes. Under highly preferred embodiments, the polyester polyol based thermoplastic urethane constituency of the layer 30 will be present in the range of between about 5.0 wt. % to about 25.0 wt. %.

Of the various materials which are considered to be useful in blended association with the polyester polyol based urethanes, copolymers of ethylene and vinyl alcohol and materials including mixtures of ethylene-vinyl alcohol copolymers are generally preferred.

Commercially available products based on copolymers of ethylene and vinyl alcohol such as SOARNOL™ which is available from the Nippon Gohsei Co., Ltd. (U.S.A.) of New York, N.Y., and EVAL® which is available from Eval Company of America, Lisle, Ill. have proven to be useful. Highly preferred commercially available copolymers of ethylene and vinyl alcohol such as EVAL® LCF101A will typically have an average ethylene content of between about 25 mol % to about 48 mol %.

Other materials useful for blending with one or more polyester polyol based urethanes as described above which are commercially available include BAREX™ 210 which is a copolymer of acrylonitrile and methyl acrylate available from the British Petroleum Co. and ISOPLAST™ which is a polyurethane engineering thermoplastic available from the Dow Chemical Co.

In addition to blending the materials selected from the group consisting of co-polymers of ethylene and vinyl alcohol, polyvinylidene chloride, co-polymers of acrylonitrile and methyl acrylate, polyethylene terephthalate, aliphatic and aromatic polyamides, crystalline polymers and polyurethane engineering thermoplastics with polyester polyol based urethanes as described above, it should be recognized by those skilled in the art that such materials can be utilized for the production of separate layers for lamination in multi-layer embodiments as described herein.

While it is generally preferred that the polyurethanes employed for both the monolayer and multi-layer embodiments are based on aromatic isocyanates such as diphenylmethane diisocyanate (MDI), in certain multi-layer constructions, it may be desirable to use aliphatic polyurethanes in combination with the above described barrier materials. More particularly, polyurethanes based on aliphatic isocyanates would preferably be employed where it is contemplated that aromatic isocyanates beyond a certain concentration would react with the barrier material employed. For example, and without intending to be limiting, when a blended layer includes a concentration of 5.0 wt. % of copolymers of ethylene and vinyl alcohol, polyurethanes based on aliphatic isocyanates would be preferred. It may, however, be beneficial to include a relatively small amount of at least one aromatic thermoplastic polyurethane (i.e. those derived from aromatic isocyanates) as a viscosity modifier. Thus, the preferred composition of a blended layer including at least 5 wt. % of at least one co-polymer of a reactive barrier material such as a co-polymer of ethylene and vinyl alcohol can be summarized as including: (a) at least 50 wt. % of at least one barrier material selected from the group consisting of co-polymers of ethylene and vinyl alcohol, polyvinylidene chloride, co-polymers of acrylonitrile and methyl acrylate, polyethylene terephthalate, aliphatic and aromatic polyamides, crystalline polymers and polyurethane engineering thermoplastics; (b) 1 wt. % to about 50 wt. % of at least one aliphatic thermoplastic urethane; and (c) up to about 3 wt. % of aromatic thermoplastic urethanes, wherein the total constituency of the blended layer is equal to 100 wt. %. The aromatic thermoplastic urethanes are also typically selected from the group consisting of polyester, polyether, polycaprolactone, polyoxypropylene and polycarbonate macroglycol based materials and mixtures thereof.

Additionally, it may be desirable under certain applications to include blends of polyurethanes to form layers 30A and 30, respectively, such as where susceptibility to hydrolysis is of particular concern. For example, a polyurethane including soft segments of polyether polyols or polyester polyols formed from the reaction mixture of a carboxylic acid and a diol wherein the repeating units of the reaction product has more than eight carbon atoms can be blended with polyurethanes including polyester polyols having eight or less carbon atoms. Preferably, the polyurethanes other than those including polyester polyol repeating units having eight or less carbon atoms will be present in the blends in an amount up to about 30 wt. %, (i.e. 70.0 wt. % polyethylene glycol adipate based urethane 30.0% isophthalate polyester polyol based urethane). Specific examples of the polyester polyols wherein the reaction product has more than eight carbon atoms include poly(ethylene glycol isophthalate), poly(1,4 butanediol isophthalate) and poly(1,6 hexanediol isophthalate).

Additionally, rather than using blends of various thermoplastic urethanes, it is also possible to utilize a single polyurethane wherein various soft segments are included therein. Again, without intending to be limiting, the soft segments may include, in addition to soft segments having a total of eight carbon atoms or less, polyether polyols, polyester polyols having a total of more than eight carbon atoms, or mixtures thereof. It is contemplated that the total amount of soft segment constituency which includes the reaction product of a carboxylic acid and a diol having a total carbon atom count of more than eight, be present in an amount of up to about 30 wt. % of the total weight of soft segments included in the polyurethane. Thus, at least 70 wt. % of the soft segment repeating units will be the reaction products of carboxylic acid and a diol, wherein the total carbon atom count for the reaction product is eight or less.

It should also be noted that there are a number of ways to add polyurethanes with up to 30 wt. % of polyesters with repeat units containing more than eight carbon atoms to the polyurethanes of this invention. Thirty percent or less of a polyurethane derived from polyester polyols containing repeat units with more than eight carbons can be blended as finished polymers with 70 wt. % or more of polyurethanes derived from polyester polyols with repeat units containing eight or less carbon atoms, or a single polyurethane could be prepared from a mixture of polyester polyols wherein 70 wt. % or more contain repeat units with eight carbons or less and the balance contains repeat units with more than eight carbons as described previously. A polyurethane could be prepared from a single polyol prepared by reaction from dicarboxylic acids and diols such that 70 wt. % of the repeat units in the polyester polyol contain eight or less carbon atoms. Combinations of these techniques are also possible. Among the acids that contain more than six carbon atoms that could be employed are isophthalic and phthalic acids.

As discussed, the membranes 28 of the present invention may also be in the form of multi-layer constructions. For example, membranes 28 and A of FIGS. 4–7 include a layer 32 formed of a flexible resilient elastomeric material which preferably is resistant to expansion beyond a predetermined maximum volume when the membrane is subjected to gaseous pressure.

The layer 32 preferably is formed of a material or combination of materials which offer superior heat sealing properties, flexural fatigue strength, a suitable modulus of elasticity, tensile and tear strength and abrasion resistance. Among the available materials which offer these characteristics, it has been found that thermoplastic elastomers of the urethane variety, otherwise referred to herein as thermoplastic urethanes or simply TPU's, are highly preferred because of their excellent processability.

Among the numerous thermoplastic urethanes which are useful in forming the outer layer 32, urethanes such as PELLETHANE™ 2355-ATP, 2355-95AE and 2355-85A (trademarked products of the Dow Chemical Company of Midland, Mich.), ELASTOLLAN® (a registered trademark of the BASF Corporation) and ESTANE® (a registered trademark of the B.F. Goodrich Co.), all of which are either ester or ether based, have proven to be particularly useful. Still other thermoplastic urethanes based on polyesters, polyethers, polycaprolactone and polycarbonate macroglycols can be employed. Further, in addition to the commercially available polyurethanes, it should also be noted that layer 32 of FIG. 4 and layers 32 and 34 of membrane A shown in FIG. 7 could also be made from the polyester polyol based polyurethanes containing soft segments wherein the reaction product has eight or less carbon atoms. This would generally result in a reduction in GTR's since much of the resistance to gas diffusion in multi-layer constructions comes from the barrier layer.

As previously noted, the membranes as disclosed herein can be formed by various processing techniques including but not limited to extrusion, blow molding, injection molding, vacuum molding and heat sealing or RF welding of tubing and sheet extruded film materials. With regard to the multi-layer membranes described herein, such membranes are made from films formed by co-extruding the material forming layer 30 together with the material comprising layer 32. After forming the multi-layered film materials, the film materials are heat sealed or welded by RF welding to form the inflatable membranes which are highly flexible in nature.

The membranes, whether in the form of sheet, substantially closed containers, cushioning devices, accumulators or other structures, preferably will have a tensile strength on the order of at least about 2500 psi; a 100% tensile modulus of between about 350–3000 psi and/or an elongation of at least about 250% to about 700%.

Figure 6:
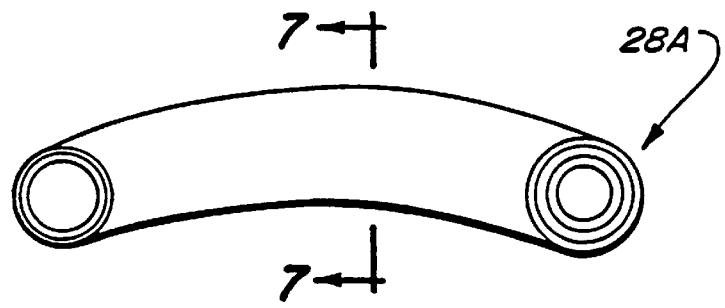
FIG. 6 is a fragmentary side perspective view of a second embodiment of a tubular-shaped, three-layer cushioning device.
Figure 7:
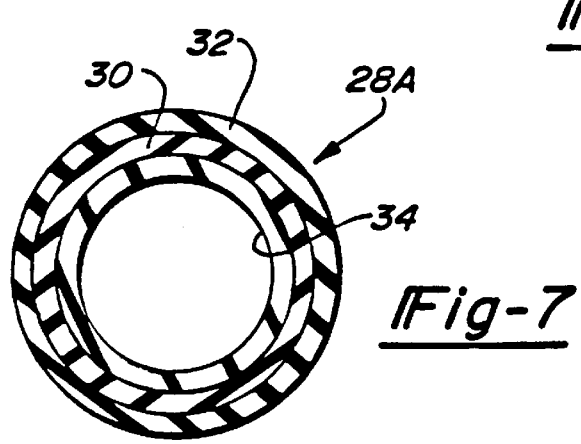
FIG. 7 is a sectional side view taken along line 6—6 of FIG. 6.

Referring now to FIGS. 6 and 7, an alternative membrane embodiment A in the form of an elongated tubular shaped multi-layered component is illustrated. The modified membrane A is essentially the same as the membrane 28 illustrated in FIGS. 4 and 5 except that a third layer 34 is provided contiguously along the inner surface of the layer 30, such that layer 30 is sandwiched between an outer layer 32 and an innermost layer 34. The innermost layer 34 is also preferably made from a thermoplastic urethane material. In addition to the perceived benefit of enhanced protection against degradation of layer 30, layer 34 also tends to assist in providing for high quality welds which facilitate the formation of three-dimensional shapes for products such as cushioning devices useful in footwear.

Membranes such as those shown in FIGS. 1–7 and FIG. 24 are preferably fabricated from extruded tubes. Lengths of the tubing which typically range from about one foot up to about five feet in length. Membranes can then be inflated to a desired initial inflation pressure ranging from 0 psi ambient to 100 psi, preferably in the range of 5 to 50 psi, with the captive gas preferably being nitrogen. Sections of the tubing are thereafter RF welded or heat sealed to the desired lengths. The individual membranes produced upon RF welding or heat sealing are then separated by cutting through the welded areas between adjacent membranes. It should also be noted that the membranes can be fabricated from so-called flat extruded tubing as is known in the art whereby the internal geometry is welded into the tube.

With regard to extruding the multi-layer embodiments described herein, as the material which forms layers 30, 32 and optionally, layer 34 advance to the exit end of the extruder through individual flow channels, once they near the die-lip exit, the melt streams are combined and arranged to float together in layers typically moving in a laminar flow as they enter the die body. Preferably, the materials are combined at a temperature of between about 300° F. to about 465° F. and a pressure of at least about 200 psi to obtain optimal wetting for maximum adhesion between the contiguous portions of the layers 30, 32 and 34 respectively and further to enhance hydrogen bonding between the layers wherein the materials employed are conducive to hydrogen bonding. Again, for multi-layered laminates, it is preferred that the polyester polyols utilized in the polyurethanes of layers 30, 32 and 34 be highly aliphatic in nature, since aliphatic urethanes have been found to be readily processable utilizing conventional techniques such as sheet extrusion.

To this end, it is believed that hydrogen bonding occurs between the respective layers as the result of available functional groups with hydrogen atoms that can participate in hydrogen bonding such as hydrogen atoms in hydroxyl groups or hydrogen atoms attached to nitrogen atoms in urethane groups and various receptor groups such as oxygen atoms in hydroxyl groups, carbonyl oxygens in urethane groups and ester groups and chlorine atoms in PVDC, for example.

The chemical reaction provided below illustrates the theoretical surface bond which is believed to occur between layers 32 and 34 with layer 30 across substantially the entire intended contact surface area of the membrane:

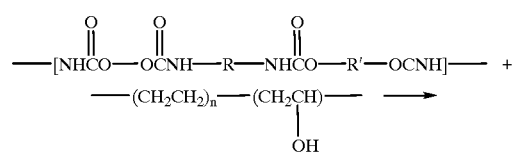

-continued

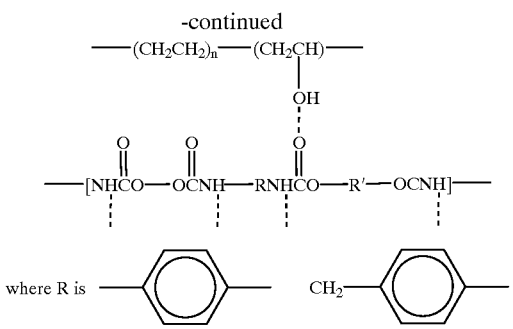

In addition to the hydrogen bonding as illustrated above, to a more limited extent, it is believed that a certain amount of covalent bonds are formed between the second and third layers 32 and 34, respectively, with the first layer 30. Still other factors such as orientation forces and induction forces, otherwise known as van der Waals forces, which result from London forces existing between any two molecules and dipole-dipole forces which are present between polar molecules are believed to contribute to the bond strength between contiguous layers of thermoplastic urethane and the main layer.

The hydrogen bonding as described above is in contrast to prior art embodiments which, failing to recognize the existence and/or potential of such bonding, typically have required the use of adhesive tie-layers such as Bynel®, for example, to maintain the bonding between the various layers.

As noted above, since fillers tend to negatively effect the so-called hydrogen bonding capacity of multi-layer embodiments, while the use of up to about 60.0 wt. % of fillers in monolayer embodiments is contemplated, the use of fillers in processing multi-layer membranes where hydrogen bonding is desired should be limited, if used at all.

Figure 12:
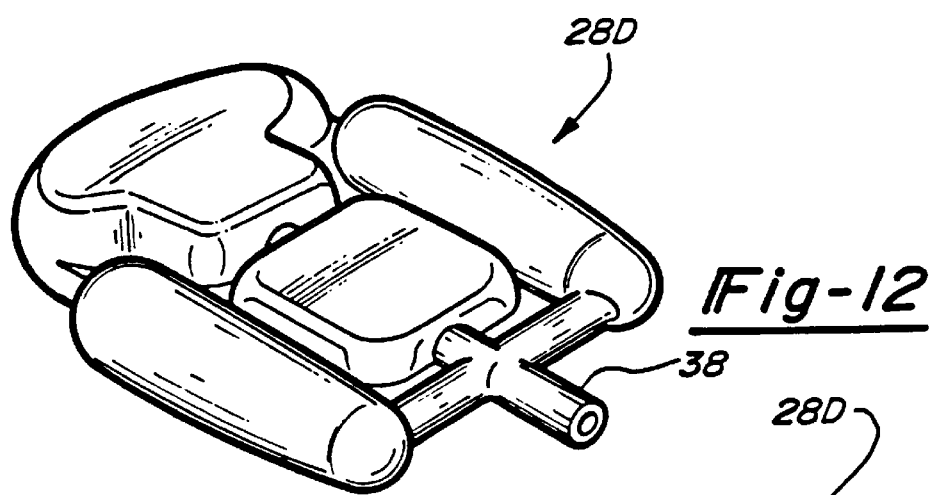
FIG. 12 is a perspective view of the membrane illustrated in FIG. 11.
Figure 13:
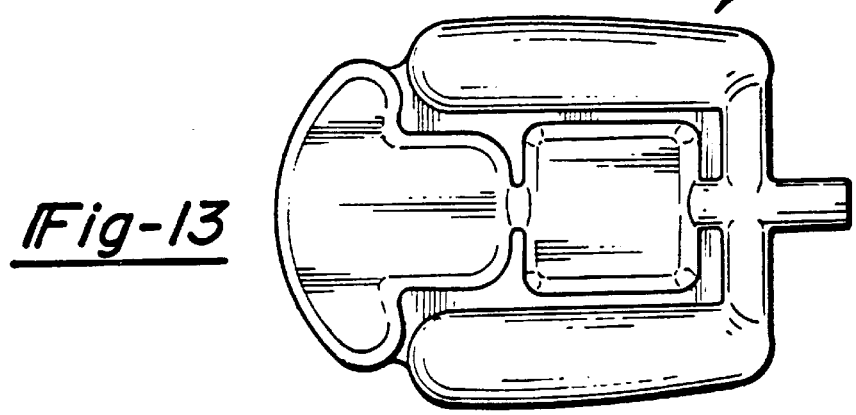
FIG. 13 is a top elevation view of the membrane illustrated in FIGS. 11 and 12.
Figure 14:
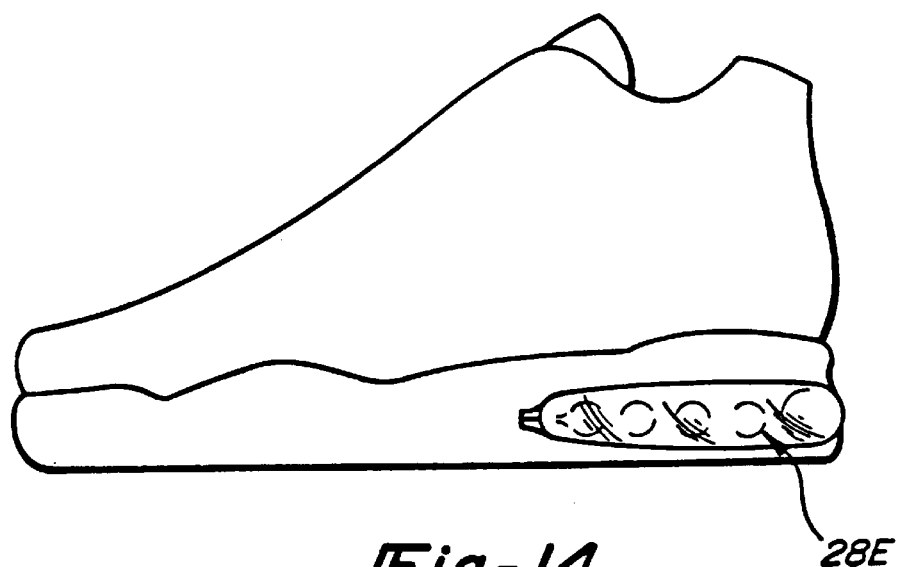
FIG. 14 is a side elevation view of a membrane embodiment according to the present invention formed into a cushioning device incorporated into a shoe.
Figure 15:
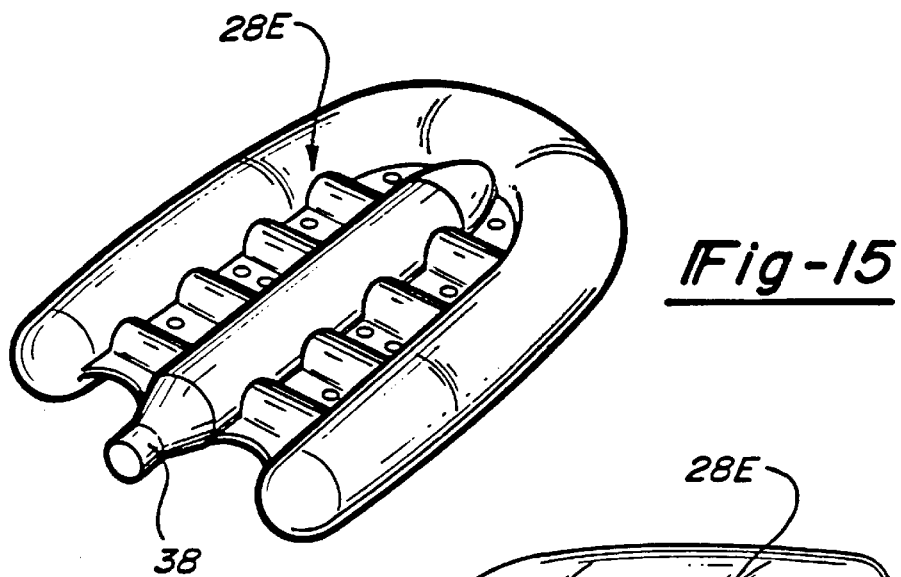
FIG. 15 is a perspective view of the membrane illustrated in FIG. 14.
Figure 16:
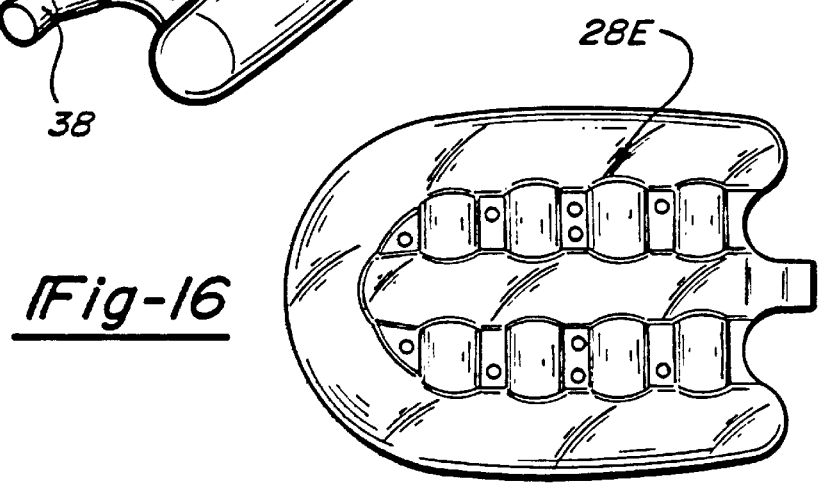
FIG. 16 is a top view of the membrane illustrated in FIGS. 14 and 15.

Referring to FIGS. 12–16, membranes in the form of air bladders are fabricated by blow molding are shown. To form the bladders, single layer parisons are extruded or parisons of two layer or three layer film are co-extruded as illustrated in FIGS. 21–23. Thereafter, the parisons are blown and formed using conventional blow molding techniques. The resulting bladders, examples of which are shown in FIGS. 12 and 15, are then inflated with the desired captive gas to the preferred initial inflation pressure and then the inflation port (e.g. inflation port 38) is sealed by RF welding.

Figure 8:
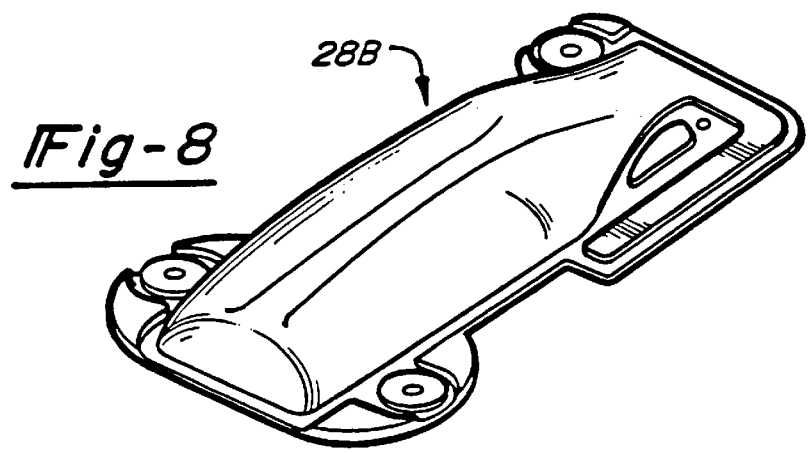
FIG. 8 is a perspective view of a membrane embodiment according to the present invention formed into a shoe cushioning device.
Figure 9:
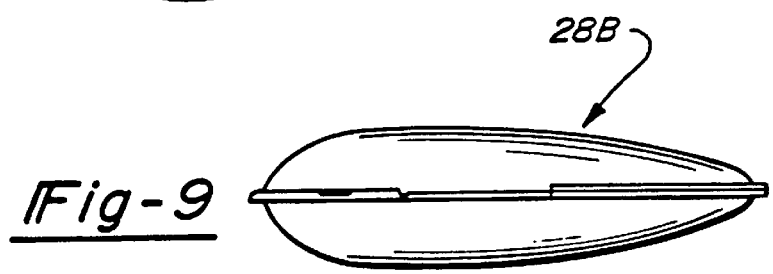
FIG. 9 is a side view of the membrane illustrated in FIG. 8.
Figure 10:
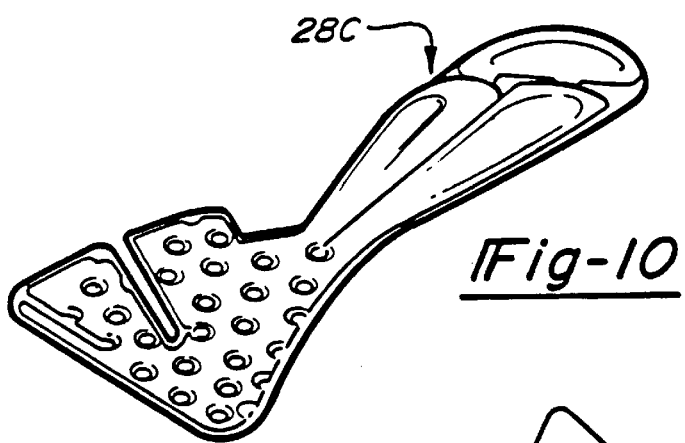
FIG. 10 is a perspective view of a membrane embodiment according to the present invention formed into a shoe cushioning device.
Figure 11:
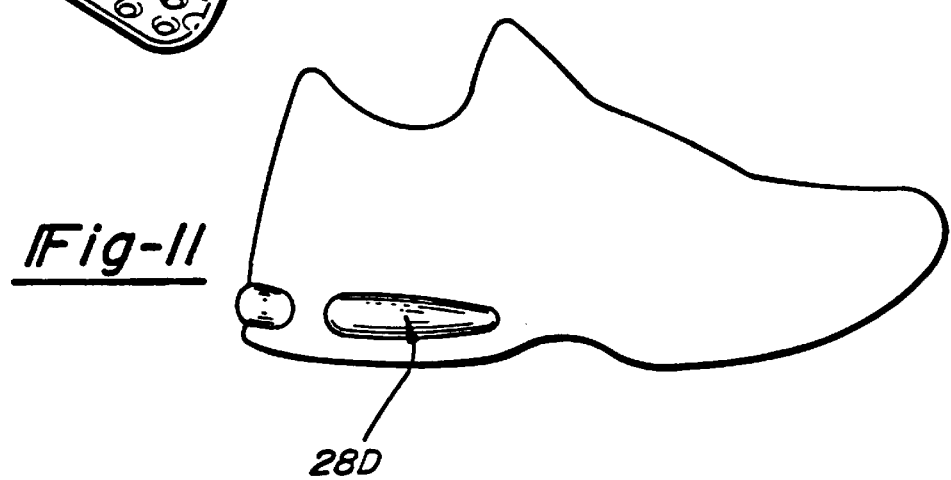
FIG. 11 is a side elevational view of a membrane embodiment according to the present invention formed into a cushioning device which is incorporated into a shoe.

Still other embodiments formed from the membranes described herein are shown in FIGS. 8–10. Sheets or films of extruded monolayer film or co-extruded two layer or three layer film are formed to the desired thicknesses. For example, the thickness range of the co-extruded sheets or films is preferably between 0.5 mils to 10 mils for the layer 30 and between 4.5 mils to about 100 mils for the layers 32 and 34, respectively. For monolayer cushioning device embodiments, the average thickness will generally be between 5 mils to about 60 mils and, more preferably, between about 15 mils and to about 40 mils.

Figure 17:
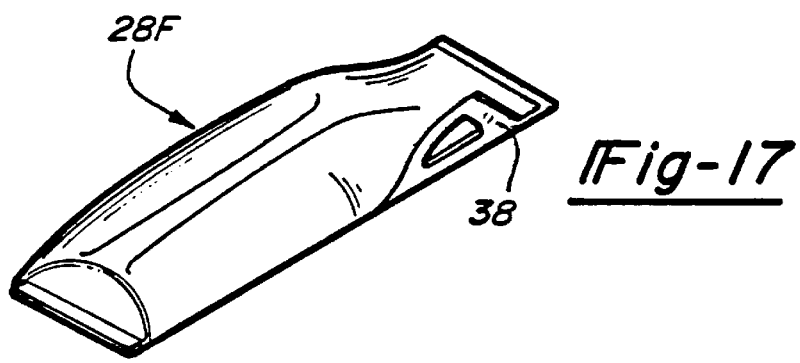
FIG. 17 is a perspective view of a membrane embodiment according to the teachings of the present invention formed into a shoe cushioning device.
Figure 18:
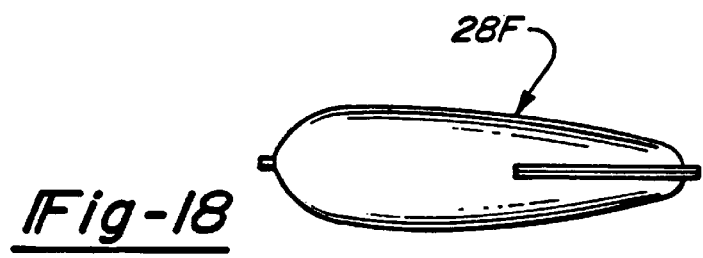
FIG. 18 is a side view of the membrane illustrated in FIG. 17.

Still another embodiment formed from a membrane of the present invention is shown in FIGS. 17 and 18. The air bladder is fabricated by forming extruded single layer or co-extruded multiple layer tubing having a desired thickness range. The tubing is collapsed to a lay flat configuration and the opposite walls are welded together at selected points and at each end using conventional heat sealing or RF welding techniques. The cushioning device is then inflated through a formed inflation port 38 to the desired inflation pressure which ranges from 0 psi ambient to 100 psi, and preferably from 5 to 50 psi, with a captive gas such as nitrogen.

Figure 25:
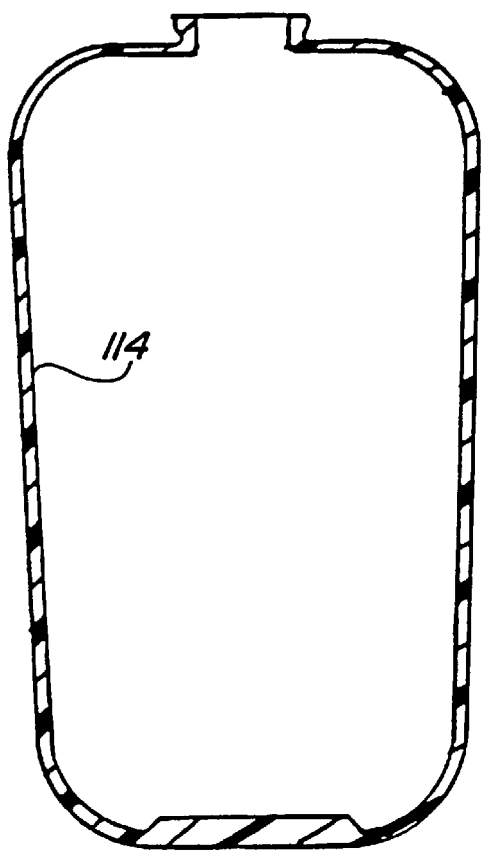
FIG. 25 is a sectional view of a product formed from a monolayer membrane according to the teachings of the present invention.

In addition to employing the membranes of the present invention as cushioning devices or air bladders as described above, still another highly desirable application for the membranes of the present invention is for accumulators as illustrated in FIGS. 19, 20 and 25.

Referring to FIG. 25, there is shown an accumulator embodiment formed from a monolayer membrane as described above. Likewise, referring to FIGS. 19 and 20, there are shown two alternative accumulator embodiments formed from a multi-layer membrane of the present invention. Accumulators, and more particularly, hydraulic accumulators are used for vehicle suspension systems, vehicle brake systems, industrial hydraulic accumulators or for other applications having differential pressures between two potentially dissimilar fluid media. The membrane 124 separates the hydraulic accumulator into two chambers or compartments, one of which contains a gas such as nitrogen and the other one of which contains a liquid. Membrane 124 includes an annular collar 126 and a flexible body portion 128. Annular collar 126 is adapted to be secured circumferentially to the interior surface of the spherical accumulator such that body portion 128 divides the accumulator into two separate chambers. The flexible body portion 128 moves generally diametrically within the spherical accumulator and its position at any given time is dependent upon the pressure of the gas on one side in conjunction with the pressure of the liquid on the opposite side.

By way of further example, FIG. 20 illustrates a product in the form of a hydraulic accumulator including a first layer 114 made from the materials described with reference to layers 30A and 30 as described above. Additionally, the product includes layers 112 and 116 formed from one or more thermoplastic urethanes, one or more barrier materials or a combination of at least one urethane and barrier material as described with reference to layers 32 and 34 above. As shown, the first layer 114 only extends along a segment of the entire accumulator body portion. It may be desirable to utilize such embodiments, otherwise referred to herein as "intermittent constructions" under circumstances where the delamination potential along certain segments of a product is greatest. One such location is along the annular collar 126 of the bladder or diaphragm for hydraulic accumulators in multi-layer embodiments. Thus, while the multi-layer membranes of the present invention are generally more resistant to delamination and do a better job of preventing gas from escaping along interfaces between layers such as those occurring along the annular collar via capillary action, it should be recognized that the membranes 110 described herein can include segments which do not include layer 114.

To form the membranes 110 which are subsequently formed into the products illustrated in FIGS. 19, 20 and 25, a number of different processes can be used, including but not limited to, extrusion and co-extrusion blow molding utilizing continuous extrusion, intermittent extrusion utilizing (1) reciprocating screw systems; (2) ram accumulator-type systems; and (3) accumulator head systems, co-injection stretch blow molding, extruded or co-extruded sheet, blown film, tubing or profiles. With regard to multi-layer processes, it has been found that utilizing co-extrusions give rise to products which appear to demonstrate the above desired hydrogen bonding between the respective layers 114 and, 112 and 116, respectively, when conducive materials are utilized. To form a product such as a hydraulic accumulator bladder or diaphragm via a multi-layer process, such as blow molding, any one of a number of commercially available blow molding machines such as a Bekum BM502 utilizing a co-extrusion head model No. BKB95-3B1 (not shown) or a Kup KEB-5 model utilizing a model No. VW60/35 co-extrusion head (not shown) could be utilized.

As previously noted, the manufacture of monolayer membranes generally resembles the manufacture of multi-layer membranes but requires far fewer process controls. For example, monolayer membranes require only a single extruder with no feed block being required. Sheet can be made by forcing molten polymer formed in the extruder through a coat hanger die. Collapsed tubing and parisons used in blow molding are made by forcing molten plastic generated by an extruder through an annular die.

A brief description of preferred multi-layer processing techniques will now be provided. Initially, the resinous materials to be extruded are first dried to the manufacturer's specification (if necessary) and fed into the extruder. Typically, the materials are fed into the extruders according to the order in which the layers are to be arranged. For example, with regard to a three layer embodiment, a material including polyester polyol based urethane is fed to an outside extruder, a material such as a TPU and/or one or more barrier materials is fed to a middle extruder and a material such as a TPU is fed to an inside extruder. The extruder heat profile is set for the best processing of the individual materials. It is suggested, however, that no more than a 20° F. difference be present at the exit point of each extruder. As the material is forced forward in each extruder, the heat profile is set to achieve the best molten mass. The heat profile would typically be set for between 300° F. to about 465° F. with the feed zone being the lowest set point and all other set points gradually increasing in increments of approximately 10° F. until the desired melt is achieved. Once leaving the extruders a section of pipes is sometimes used to direct the material to the multi-layered head (i.e. three or more heads). It is at this point that any adjustments for differences in heat are addressed. The pumping action of the extruders not only forces the material into the individual head channels or flow paths but also determines the thickness of each layer. As an example, if the first extruder has a 60 mm diameter, the second extruder has a 35 mm diameter and the third extruder has a 35 mm diameter, the speeds required to produce a 1.3 liter bladder or diaphragm requiring 2 mm for the outside layer, 3 mils for the middle layer and 2 mm for the inside layer for the various extruder would be approximately 26 seconds for the first extruder having a screw speed of about 10 rpm's, the second extruder would have a screw speed of about 5 rpm's and the third extruder would have a screw speed of about 30 rpm. Once the materials enter the head channels or flow paths, the heat would normally be held constant or be decreased to adjust for the melt strength of the materials. The individual head channels or flow paths keep separate the molten masses while directing them downward and into the shape of a parison.

Just prior to entering the lower die or bushing and the lower mandrel, the material head channels or flow paths are brought together under the pressure created by the now unitary flow path surface area, the gap between the lower bushing and mandril and the pressure on the individual layers from the respective extruders. This pressure must be at least 200 psi and is normally, under the conditions described, in excess of 800 psi. At the point where the materials come together, one parison is now formed that is a laminate made up of the three layers. The upper limit of the pressure is essentially only constrained by the physical strength of the head. After exiting the head, the laminate is closed on each end by the two mold halves and a gas such as air is injected into the mold forcing the laminated parison to blow up against the mold and be held in this fashion until sufficient cooling has taken place (i.e. approximately 16 seconds for the aforementioned sample), at which point the gas is exhausted. The part is then removed from the mold and further cooling is allowed for sufficient time to allow for the part to be de-flashed or further processed as some parts may require. As should now be understood by those skilled in the art, the layers must be held separate until fully melted and preformed into a hollow tube at which time they are bonded together under the heat and pressure described herein.

As those skilled in the plastic forming industry will recognize, the three major components of a blow molding machine, namely the extruders, die heads and mold clamps, come in a number of different sizes and arrangements to accommodate for the consumer production rate schedule and size requirements.

A multi-layer process known as sheet co-extrusion is also a useful technique to form membranes in accordance with the teachings of the present invention. Sheet co-extrusion generally involves the simultaneous extrusion of two or more polymeric materials through a single die where the materials are joined together such that they form distinct, well bonded layers forming a single extruded product.

The equipment required to produce co-extruded sheet consists of one extruder for each type of resin which are connected to a co-extrusion feed block such as that shown in FIGS. 21 and 23, which are commercially available from a number of different sources including the Cloreon Company of Orange, Tex. and Production Components, Inc. of Eau Claire, Wis., among others.

The co-extrusion feed block 150 consists of three sections. The first section 152 is the feed port section which connects to the individual extruders and ports the individual round streams of resin to the programming section 154. The programming section 154 then reforms each stream of resin into a rectangular shape the size of which is in proportion to the individual desired layer thickness. The transition section 156 combines the separate individual rectangular layers into one square port. The melt temperature of each of the TPU layers should generally be between about 300° F. to about 465° F. To optimize adhesion between the respective layers, the actual temperature of each melt stream should be set such that the viscosities of each melt stream closely match. The combined laminar melt streams are then formed into a single rectangular extruded melt in the sheet die 158 which preferably has a "coat hanger" design as shown in FIG. 22 which is now commonly used in the plastics forming industry. Thereafter the extrudate can be cooled utilizing rollers 160 forming a rigid sheet by either the casting or calendaring process.

Similar to sheet extrusion, the equipment required to produce co-extruded tubing consists of one extruder for each type of resin with each extruder being connected to a common multi-manifolded tubing die. The melt from each extruder enters a die manifold such as the one illustrated in FIG. 23 which is commercially available from a number of different sources including Canterberry Engineering, Inc. of Atlanta, Ga. and Genca Corporation of Clearwater, Fla. among others, and flows in separate circular flow channels 172A and 172B for the different melts. The flow channels are then shaped into a circular annulus the size of which is proportional to the desired thickness for each layer. The individual melts are then combined to form one common melt stream just prior to the die entrance 174. The melt then flows through a channel 176 formed by the annulus between the outer surface 178 of a cylindrical mandrel 180 and the inner surface 182 of a cylindrical die shell 184. The tubular shaped extrudate exits the die shell and then can be cooled into the shape of a tube by many conventional pipe or tubing calibration methods. While a two component tube has been shown in FIG. 23 it should be understood by those skilled in the art that additional layers can be added through separate flow channels.

Regardless of the plastic forming process used, it is desirable that a consistent melt of the materials employed be obtained to accomplish bonding between layers across the intended length or segment of the laminated product. Again then, the multi-layer processes utilized should be carried out at maintained temperatures of from about 300° F. to about 465° F. Furthermore, it is important to maintain sufficient pressure of at least 200 psi at the point where the layers are joined wherein the above described hydrogen bonding is to be effectuated.

As previously noted, in addition to the excellent bonding which can be achieved for the laminated membrane embodiments of the present invention, another objective, especially with regard to membranes employed as cushioning devices for footwear, is to provide membranes which are capable of retaining captive gases for extended periods of time. In general, membranes which offer gas transmission rate values of 15.0 or less for nitrogen gas as measured according to the procedures designated at ASTM D-1434-82 for membranes having an average thickness of 20 mils are acceptable candidates for extended life applications. Thus, while the membranes of the present invention can have varying thicknesses depending mainly on the intended use of the final product, the membranes of the present invention will preferably have a gas transmission rate value of 15.0 or less when normalized to a thickness of 20 mils regardless of the actual thickness of the membrane. Likewise, while nitrogen gas is the preferred captive gas for many embodiments and serves as a benchmark for analyzing gas transmission rates in accordance with ASTM D-1434-82, the membranes can contain a variety of different gases and/or liquids.

In this regard, because of the excellent characteristics offered by the polyester polyol based urethanes in terms of flexibility, resistance to degradation caused by moisture and resistance to undesired gas transmissions, among others, the membranes of the present invention can be employed as either monolayer or multi-layer embodiments. Under preferred embodiments, the membranes of the present invention will have a gas transmission rate of 10.0 and still, more preferably, will have gas transmission rates of 7.5 or less for nitrogen gas at 20 mils. Still more preferably, the membranes of the present invention will have a gas transmission rate of 5.0 or less and, still more preferably yet, will have a gas transmission rate of 2.5 or less for nitrogen gas at 20 mils. Under the most highly preferred embodiments, the membranes of the present invention will have a gas transmission rate of 2.0 or less for nitrogen gas for membranes having an average thickness of 20 mils.

To prepare Samples 1–12 as set forth in Table I for gas transmission rate analysis, the polyester polyol based urethane was initially prepared by adding one or more of the following constituents to a 2000 ml reaction flask: (1) polyester polyol (i.e. commercial product or reaction product of dicarboxylic acid and diol, as described); (2) difunctional extender; and (3) processing aids such as waxes and antioxidants. Thereafter, the hydroxyl component was heated to between approximately 95° C.–115° C. (depending on the composition) and stirred to dissolve and homogenize the constituents. Subsequently, a vacuum of less than 0.2 mm Hg was applied under constant stirring to control foaming. After foaming was completed, the flask was degassed for approximately 30 minutes until virtually all bubbling ceased.

Next, the isocyanate component was prepared by disposing a diisocyanate in a 250 ml polypropylene beaker and placing the diisocyanate in an oven heated to between approximately 50–65° C. Upon obtaining a temperature of between about 50–65° C., the desired amount of the isocyanate constituent was weighted out and the catalyst, if any, was added to the isocyanate constituent under constant mixing.

Once the catalyst was fully mixed in, the desired amount of hydroxyl component was added to the isocyanate component to effectuate polymerization. As polymerization began and the viscosity increased (generally between about 7–12 seconds after addition), the reaction product was poured into pans coated with a desirable release agent and allowed to fully cool. Upon cooling, the newly formed polymer was cut into granules and dried for approximately 2–4 hours at between 85–100° C. Thereafter, Samples 1–10, as set forth in Table I, were prepared by compression molding granules of plastic into sheets to conduct analysis relating to gas transmission properties.

With regard to Sample 11 as illustrated in Table I, after forming the polyester polyol based urethane as described above, 70.0 wt. % of the material was blended and extruded along with the 30.0 wt. % BAREX™ 210 available from BP Chemical, Inc., at a temperature of approximately 420° F. to provide a blended sample for gas transmission analysis. Further, with regard to Sample 12, a membrane was formed for gas transmission analysis by blending 70.0 wt. % of the polyester polyol based urethane set forth in Sample 12 with 30.0 wt. % of the BAREX™ 210 at a temperature of approximately 420° F.

TABLE I*

Gas Transmission Rates For Single Layers

| Formulation | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Polybutanediol Adipate | | | | | | | | | | | | | | |
| (a) 2000 m.w.[1] | 43.12 | | | | | | | | | | | | | |
| (b) 700 m.w.[2] | 15.09 | | | | | | | | | | | | | |
| Ethylene Glycol Adipate | | | | | | | | | | | | | | |

TABLE I*-continued

| Formulation | Gas Transmission Rates For Single Layers | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| (a) 1000 m.w.[3] | | 61.11 | 62.29 | 49.18 | 60.63 | 49.60 | 30.26 | 16.39 | | 42.84 | 51.23 | | | |
| (b) 500 m.w.[4] | | | | | | | 22.69 | 32.77 | | | | | | |
| HD Adipate/HD Isophthalate (a) 1000 m.w.[5] | | | | | | | | | | | 18.36 | | | |
| Ethylene Glycol Glutarate (a) 1000 m.w.[6] | | | | | | | | | | 51.23 | | | | |
| Ethylene Glycol | | | 4.25 | | | | | | | | | | | |
| Dipropylene glycol | 0.58 | | | | | | | | | | | | | |
| Butyl Carbitol | 0.21 | | | | | | | | 0.25 | | 0.25 | | | |
| 1,4 Butanediol | 7.37 | 6.05 | | 9.96 | 6.00 | 8.93 | 6.81 | 7.37 | 9.22 | 6.06 | 9.22 | | | |
| H12MDI[7] | | | | | | 41.07 | 39.84 | | | | | | | |
| MDI[8] | 33.04 | 32.5 | | 40.52 | | | | 43.15 | 38.96 | 32.40 | 38.96 | | | |
| MDI/liq. MDI[9] | | | 33.12 | | 33.03 | | | | | | | | | |
| Irganaox 1010[10] | 0.125 | 0.15 | 0.15 | 0.15 | 0.15 | 0.15 | 0.15 | 0.15 | 0.15 | 0.15 | 0.15 | | | |
| Advawax 280[11] | 0.125 | 0.15 | 0.15 | 0.15 | 0.15 | 0.15 | 0.15 | 0.15 | | 0.15 | | | | |
| Wax[12] | 0.30 | | | | | | | | 0.15 | | | | | |
| Catalyst[13] | 0.04 | 0.04 | 0.04 | 0.04 | 0.04 | 0.10 | 0.10 | 0.02 | 0.04 | 0.04 | 0.04 | | | |
| Kemamide W-40[14] | | | | | | | | | | | 0.15 | | | |
| Pellethane 2355-85 ATP[15] | | | | | | | | | | | | 100.0 | 100.0 | |
| Pellethane 2355-95 AE[16] | | | | | | | | | | | | | | 100.0 |
| Total Wt. % | 100.0 | 100.0 | 100.0 | 100.0 | 100.0 | 100.0 | 100.0 | 100.0 | 100.0 | 100.0 | 100.0 | 100.0 | 100.0 | 100.0 |

*All values provided in Table I are in weight percents (wt. %)
[1]FOMREZ ™ 56 available from Witco Chemical
[2]FOMREZ ™ 160 available from Witco Chemical
[3]FOMREZ ™ 22-112 available from Witco Chemical
[4]FOMREZ ™ 22-225 available from Witco Chemical
[5]FOMREZ ™ 8066-120 - 50 parts 1,6 hexanediol adipate and 50 parts HD Isophthalate polyester polyol available from Witco Chemical
[6]UrethHall ™ 2050 available from C. P. Hall Company
[7]DESMODUR W available from BAYER AG (America)
[8]ISONATE ™ 2125M available from Dow Chemical Co.
[9]Blend of 80 parts ISONATE ™ 2125 and 20 parts ISONATE ™ 2143 available from Dow Chemical Co.
[10]IRGANOX ™ 1010 available from Ciba-Gigy Chemical Co.
[11]ADVAWAX ™ 280 available from Morton Plastics, Inc.
[12]Montan ester wax
[13]Blend of 50 parts stannous octoate and 50 parts dioctyl phthalate
[14]Kemamide W-40 (ethylene bis-stearamide wax) available from Witco Chemical
[15]PELLETHANE ™ 2355-85 ATP available from Dow Chemical Co.
[16]PELLETHANE ™ 2355-95 AE available from Dow Chemical Co.

TABLE II

| Sample Number | Average Thickness | GTR (cc/m$^2$ * atm * day) | GTR (cc/m$^2$ * atm * day) Normalized to 20 mils thickness |
|---|---|---|---|
| 1 | 16.25 mils | 30.95 | 25.15 |
| 2 | 15.2 mils | 11.71 | 8.9 |
| 3 | 17.13 mils | 9.13 | 7.82 |
| 4 | 18.49 mils | 6.58 | 6.08 |
| 5 | 17.54 mils | 7.07 | 6.19 |
| 6 | 19.93 mils | 9.22 | 9.19 |
| 7 | 19.93 mils | 6.19 | 6.17 |
| 8 | 18.31 miis | 1.20 | 1.10 |
| 9 | 16.93 mils | 3.47 | 2.93 |
| 10 | 14.47 mils | 17.92 | 12.96 |
| 11 | 19.22 mils | 1.24 | 1.19 |
| 12 | 17.1 mils | 2.73 | 2.33 |
| 13 | 19.95 mils | 36.42 | 36.33 |
| 14 | 18.25 mils | 24.12 | 22.01 |

As illustrated in Table II, each of the Samples 2–12 demonstrated better gas transmission rate results than the control Samples 13–14, which were formed of commercially available thermoplastic urethane resins. Each of the samples, namely Samples 2–10 which relate to polyethylene glycol adipate and ethylene glycol glutarate based urethanes and Samples 11–12 which relate to polyethylene glycol adipate based urethane blends, including BAREX™ 210, generally demonstrated better gas transmission rate values than the polybutanediol adipate based urethane of Sample 1. As illustrated, each of the Samples 2–12, exhibited a gas transmission rate of less than 15.0 for $N_2$ at 20 mils.

A multi-layer sample was also prepared by laminating two layers of the polyester polyol based urethane as set forth in Sample 11 of Table I along with a third layer of commercially available material known as ISOPLAST™. To laminate the multi-layer sample, a sheet of 5 mil ISOPLAST™ film was sandwiched between two layers of the polyester polyol based urethane, each having a thickness of 19 mils. The multi-layer sample was then pressed within a hydraulic press having upper and lower platens heated to about 420° F. The films were pressed together at a pressure of about 2,000 psig to give rise to a sample having an overall thickness of approximately 18.25 mils.

Upon conducting the gas transmission rate analysis on the multi-layer sample, it was discovered that the sample had a GTR of 8.87 for nitrogen at 18.25 mils and as normalized to 20.0 mils had a GTR of 8.09. Thus, the multi-layer sample also met the objective of a gas transmission rate of less than 15.0.

Finally, in addition to the monolayer and multi-layer membrane samples as set forth above, a thermoset version of a polyester polyol based urethane was also prepared and analyzed for gas transmission.

The sample, as set forth in Table III below, was prepared by dehydrating and degassing the polyester polyol under a vacuum for two hours at 100° C. and cooled to 60° C. at which time the catalyst was added. Concurrently, the Isonate™ 2143L was heated to 45° C. and degassed for twenty minutes before its addition to the polyester component. The polyester polyol and polyisocyanate were then mixed and stirred carefully in a polypropylene beaker to avoid the introduction of air. Upon mixing, the mixture was cast into a warm plaque mold where it was allowed to cure for two hours at ambient temperature and pressure before demolding. The resulting membrane was allowed to remain at ambient conditions for seven days prior to testing.

TABLE III

| | |
|---|---|
| Ethylene glycol adipate (a) 1000 m.w.[1] | 77.36 |
| MDI[2] | 22.34 |
| Catalyst[3] | 0.30 |
| | 100.0 |

[1]. FOMREZ ™ 22-225 available from Witco Chemical
[2]. ISONATE ™ 2143L which is a liquid MDI available from Dow Chemical Co. of Midland, MI.
[3]. COCURE ™ 55 which is available from Caschem Inc., of Bayonne, N.J.

The thermoset version of the polyester polyol based urethanes as set forth in Table III exhibited a gas transmission rate of 3.07 for a 73 mils thickness. Upon normalizing, the gas transmission rate was calculated to be 11.2 for $N_2$ based on a 20 mil thickness. Thus, both thermoplastic and thermoset materials appear to be useful in accordance with the teachings of the present invention.

In addition to the improved resistance to gas transmission offered by the various products formed from the polyester polyol based urethanes described herein, products made from polyester polyol based urethanes have also shown a marked improvement in durability over thermoplastic urethanes which do not include polyester polyols.

For example, as illustrated in Table IV below, multiple samples were prepared and analyzed for durability utilizing a test method known as as a KIM test. In accordance with the KIM test procedures, two sheets were extruded from dffering materials with each sheet being formed into identically shaped cushioning device components having an average wall thickness of 18 mils. The material utilized for the Set A cushioning devices is the same as that set forth in Table I as Formulation No. 11. The Set B cushioning devices were made from a material such as Pellethane 2355-85A, a thermoplastic urethane that does not contain any polyethylene glycol adipate soft segments.

Upon inflating the cushioning devices to 20.0 psig with nitrogen gas, each sample was intermittently compressed by a reciprocating piston having a 4.0 inch diameter platen. The stroke of each piston was calibrated to travel a height which would compress each sample to an average of 25.0% of the initial inflated height at maximum stroke. The reciprocating pistons were then allowed to cycle or stroke until a part failure was detected. Part failure, as the term is used herein, is defined as a sufficient leakage of the nitrogen gas and deflation of the cushioning device to cause a lever placed in identical locations along each of the cushioning devices to contact a microswitch which stops the reciprocating piston stroke. The total number of cycles or strokes were then recorded for each sample with a high number of strokes being indicative of a more durable material. Preferably, permanently inflated cushioning devices should be capable of withstanding at least about 200,000 cycles to be considered for applications as footwear components.

As can be seen from a review of Table IV, the cushioning devices of Set A formed from the polyester polyol based urethane outperformed the cushioning devices formed from the aromatic thermoplastic based urethane of Set B by over three times as many cycles. Thus, the polyester polyol based urethanes utilized under the present invention not only offer better resistance to undesired gas transmission, but also have been shown to offer enhanced durability over thermoplastic urethanes which do not include polyester polyol soft segments having eight or less carbon atoms having eight or less carbon atoms in the repeating units.

TABLE IV

| Sample No. | Avg No. of Cycles |
|---|---|
| Set A* | 754, 111 |
| Set B** | 217, 797 |

*Average of 9 tests
**Average of 10 tests

In addition to a high degree of durability, it is often desirable to form products which are relatively transparent in nature, i.e. products which meet certain standards in terms of the yellowness level detected and the transmission of light through the material. For example, transparency of the product is often a consideration for cushioning devices such as those utilized as components of footwear wherein the cushioning device is visually accessible.

In this regard, cushioning devices formed from Pellethane 2355-87 ATP, an aromatic thermoplastic based urethane, have proven to be useful for shoe components since the material has been shown to offer acceptable levels both in terms of the yellowness level detected and the light transmission through the material. Thus, polyester polyol based urethanes would preferably have similar and, more preferably, improved transparency characteristics as compared to aromatic thermoplastic urethanes such as Pellethane 2355-87 ATP, among others.

Samples of both Pellethane 2355-87 ATP and a polyester polyol based urethane including: 50.96 wt. % FOMREZ 22-122 (1000 m.w.); 9.11 wt. % 1,4 Butanediol; 38.81 wt. % ISONATE 2125M; 0.50 wt. % IRGANOX 1010; 0.15 wt. % ADVAWAX 280; 0.30 wt. % montan ester wax; and 0.02 wt. % catalyst, were prepared by extruding smooth sided, collapsed tubes having an average wall thickness of 32 mils. Each sample was thereafter analyzed for its yellowness index and the total transmission of light therethrough utilizing a Hunter Lab Color QUEST™ Spectocolorimeter in accordance with the instrument's instruction manual.

The yellowness index readings were standardized in the {rsin} mode, and readings were taken along the reflectance port. The total transmission measurements were also standardized and the measurements were taken by readings without glass slides along the transmission ports.

The Pellethane 2355-87ATP had a yellowness index of 4.00 and a total transmission of light of 90.85% based on a maximum value of 100.0% transmission. The polyester polyol based urethane had a yellowness index of 1.52 and a total transmission of light of 91.75%. The polyester polyol based urethanes, thus, not only appear to be more durable than aromatic thermoplastic based urethanes but also appear to offer better values both in terms of a lower yellowness index and a higher light transmission. This improvement in terms of both decreased yellowness and an increased transmission of light should enhance the aesthetic characteristics of many final products.

While the above detailed description describes the preferred embodiment of the present invention, it should be understood that the present invention is susceptible to modification, variation and alteration without deviating from the scope and fair meaning of the subjoined claims.

What is claimed is:

1. A flexible membrane comprising:
   a polyurethane including a polyester polyol, said membrane having a gas transmission rate of 15.0 or less for nitrogen gas; wherein said membrane is sealed and in an inflated state.

2. The membrane according to claim 1, wherein said polyester polyol of said polyurethane is selected from the group consisting of the reaction product of (a) a carboxylic acid having six or less carbon atoms and (b) a diol having six or less carbon atoms, wherein the repeating units of the polyester polyol formed by the aforesaid reaction has eight carbon atoms or less.

3. The membrane according to claim 2, wherein the carboxylic acid is selected from the group consisting of adipic, glutaric, succinic, malonic and oxalic acids, and mixtures thereof.

4. The membrane according to claim 3, wherein the carboxylic acid employed includes adipic acid.

5. The membrane according to claim 2, wherein the diol is selected from the group consisting of ethylene glycol, propanediol, butanediol, neopentyldiol, pentanediol, hexanediol and mixtures thereof.

6. The membrane according to claim 5, wherein the diol employed includes ethylene glycol.

7. The membrane according to claim 2, wherein said polyurethane further comprises at least one extender.

8. The membrane according to claim 7, wherein said extender is selected from the group consisting of alcohols and amines.

9. The membrane according to claim 7, wherein said extender is selected from the group consisting of ethylene glycol, 1,3 propylene glycol, 1,4-butanediol and 1,6-hexanediol.

10. The membrane according to claim 7, wherein said at least one extender and said at least one polyester polyol include active hydrogen containing groups.

11. The membrane according to claim 7, wherein the ratio of polyester polyol to extender is between about 1:0 to about 1:12.

12. The membrane according to claim 11, wherein the ratio of polyester polyol to extender is between about 1:1 to about 1:8.

13. The membrane according to claim 10, wherein the ratio of isocyanate contained in said polyurethane to active hydrogen containing groups is between about 0.95:1 to about 1.10:1.

14. The membrane according to claim 13, wherein the ratio of isocyanate to active hydrogen containing groups is between about 0.98:1 to about 1.04:1.

15. The membrane according to claim 2, further comprising a hydrolytic stabilizer.

16. The membrane according to claim 15, wherein said hydrolytic stabilizer is present in an amount of up to 5.0 wt. %.

17. The membrane according to claim 15, wherein said hydrolytic stabilizer is selected from the group consisting of carbodiimides, polycarbodiimides and epoxidized soy bean oil.

18. The membrane according to claim 2, wherein said polyurethane includes at least one plasticizer, said plasticizer being present in an amount of up to 40.0 wt. %.

19. The membrane according to claim 2, wherein said polyurethane includes at least one flame retardant, said flame retardant being present in an amount of up to 40.0 wt. %.

20. The membrane according to claim 2, wherein said polyurethane includes at least one filler, said filler being present in an amount of up to 60 wt. %.

21. The membrane according to claim 2, wherein at least one additive is employed, said additive being selected from the group consisting of antioxidants, ultra-violet stabilizers, thermal stabilizers, light stabilizers, organic anti-block compounds, colorants, fungicides, mold release agents and lubricants, said at least one additive being present in an amount of up to 3.0 wt. %.

22. The membrane according to claim 2, further comprising at least one triol.

23. The membrane according to claim 22, wherein said at least one triol includes trimethyol propane.

24. The membrane according to claim 2, further comprising at least one material selected from the group consisting of co-polymers of ethylene and vinyl alcohol, polyvinylidene chloride, co-polymers of acrylonitrile and methyl acrylate, polyethylene terephthalate, aliphatic and aromatic polyamides, crystalline polymers and polyurethane engineering thermoplastics, said material being blended with said polyurethane prior to forming said membrane.

25. The membrane according to claim 24, wherein said membrane includes up to about 70.0 wt. % polyester polyol based urethane.

26. The membrane according to claim 25, wherein said membrane includes between about 5.0 wt. % to about 25.0 wt. % polyester polyol based urethane.

27. The membrane according to claim 24, wherein said material selected from said group includes at least one copolymer of ethylene and vinyl alcohol.

28. The membrane according to claim 27, wherein at least one of the copolymers of ethylene and vinyl alcohol has an ethylene content of between about 25 mol. % to about 48 mol. %.

29. The membrane according to claim 2, wherein said membrane includes at least one polyurethane including soft segments selected from the group consisting of polyether polyols, polyester polyols formed from the reaction product of a carboxylic acid and a diol wherein the repeating units of the reaction product have more than eight carbon atoms, or mixtures thereof.

30. The membrane according to claim 29, wherein said at least one polyurethane including soft segments selected from the group consisting of polyether polyols, polyester polyols formed from the reaction product of a carboxylic acid and a diol wherein the repeating units of the reaction product have more than eight carbon atoms, or mixtures thereof, is present in an amount of up to 30.0 wt. %.

31. The membrane according to claim 29, wherein the polyurethane including the polyester polyol formed from a carboxylic acid and a diol wherein the reaction product has more than eight carbon atoms is selected from the group consisting of ethylene glycol isophthalate, 1,4 butanediol isophalate and 1,6 hexanediol isophthalate.

32. The membrane according to claim 1, wherein said gas transmission rate is less than about 10.0 for nitrogen gas.

33. The membrane according to claim 32, wherein said gas transmission rate is less than about 7.5 for nitrogen gas.

34. The membrane according to claim 33, wherein said gas transmission rate is less than about 5.0 for nitrogen gas.

35. The membrane according to claim 34, wherein said gas transmission rate is less than about 2.5 for nitrogen gas.

36. The membrane according to claim 35, wherein said gas transmission rate is less than about 2.0 for nitrogen gas.

37. The membrane according to claim 1, wherein said membrane is elastomeric.

38. The membrane according to claim 37, wherein said membrane has an elongation of at least about 250%.

39. The membrane according to claim 38, wherein said membrane has a elongation of between 250% to about 700%.

40. The membrane according to claim 37, wherein said membrane has a tensile strength of at least about 2,500 psi.

41. The membrane according to claim 37, wherein said membrane has an 100% tensile modulus of between 350 to about 3,000 psi.

42. The membrane according to claim 1, wherein said membrane has a durometer hardness ranging from about 60 Shore A to about 65 Shore D.

43. The membrane according to claim 42, wherein said membrane has a durometer hardness ranging from about 80 Shore A to about 55 Shore D.

44. The membrane according to claim 43, wherein said membrane has a durometer hardness ranging from about 85 Shore A to about 50 Shore D.

45. The membrane according to claim 1, wherein said polyurethane is prepared from an isocyanate that is aromatic in nature.

46. The membrane according to claim 45, wherein said isocyanate is diphenylmethane diisocyanate.

47. The membrane according to claim 1, wherein said polyurethane includes:
(a) at least 50 wt. % of at least one barrier material selected from the group consisting of co-polymers of ethylene and vinyl alcohol, polyvinylidene chloride, co-polymers of acrylonitrile and methyl acrylate, polyethylene terephthalate, aliphatic and aromatic polyamides, crystalline polymers and polyurethane engineering thermoplastics, said at least one barrier material being blended with said polyurethane prior to forming said membrane;
(b) 1 wt. % to about 50 wt. % of at least one aliphatic thermoplastic urethane; and
(c) up to about 3 wt. % of one or more aromatic thermoplastic urethanes, wherein the total constituency of the blended layer is equal to 100 wt. %.

48. The membrane according to claim 47, wherein said aromatic thermoplastic urethane is selected from the group consisting of polyester, polyether, polycaprolactone, polyoxypropylene and polycarbonate macroglycol based materials and mixtures thereof.

49. The membrane according to claim 47, wherein said thermoplastic is based on aromatic 1,4,diphenylmethane diisocyanate.

50. The membrane according to claim 1, wherein said membrane forms a first layer of a multi-layer structure.

51. The membrane according to claim 50, further comprising a second layer formed from a material selected from the group consisting of co-polymers of ethylene and vinyl alcohol, polyvinylidene chloride, co-polymers of acrylonitrile and methyl acrylate, polyethylene terephthalate, aliphatic and aromatic polyamides, crystalline polymers, polyurethane engineering thermoplastics and mixtures thereof which is bonded to said first layer.

52. The membrane according to claim 51, wherein said first and second layers are formed together such that hydrogen bonding occurs between said first and second layers.

53. The membrane according to claim 1, wherein said membrane is formed at least in part from a thermoset material.

54. A flexible membrane comprising:
a polyurethane including a polyester polyol, said membrane having a durability of at least 200,000 cycles under a KIM test analysis; wherein said membrane is sealed and in an inflated state.

55. The membrane according to claim 54, wherein said membrane has a durability of more than 750,000 cycles under a KIM test analysis.

56. A flexible membrane comprising:
a polyurethane including a polyester polyol, said membrane having a yellowness index of 4.0 or less; wherein said membrane is sealed and in an inflated state.

57. The membrane according to claim 56, wherein said yellowness index is 1.6 or less.

58. A flexible membrane comprising:
a polyurethane including a polyester polyol, said membrane having a total transmission of light at a level of at least 90.0%; wherein said membrane is sealed and in an inflated state.

59. A membrane according to claim 1, wherein said membrane has an average thickness of from about 5 mils to about 200 mils.

60. A membrane according to claim 1, wherein said membrane has an average thickness of from about 5 mils to about 60 mils.

61. A membrane according to claim 1, wherein said membrane has an average thickness of from about 15 mils to about 40 mils.

\* \* \* \* \*